(12) United States Patent
Koganov

(10) Patent No.: US 8,101,212 B2
(45) Date of Patent: Jan. 24, 2012

(54) BIOACTIVE BOTANICAL COSMETIC COMPOSITIONS AND PROCESSES FOR THEIR PRODUCTION

(75) Inventor: Michael Koganov, White Plains, NY (US)

(73) Assignee: Akzo Nobel Surface Chemistry LLC, Chicago, IL (US)

(*) Notice: Subject to any disclaimer, the term of this patent is extended or adjusted under 35 U.S.C. 154(b) by 225 days.

(21) Appl. No.: 12/116,924

(22) Filed: May 7, 2008

(65) Prior Publication Data

US 2009/0017144 A1 Jan. 15, 2009

Related U.S. Application Data

(62) Division of application No. 10/351,910, filed on Jan. 24, 2003, now Pat. No. 7,442,391.

(60) Provisional application No. 60/351,886, filed on Jan. 25, 2002.

(51) Int. Cl.
*A61K 36/00* (2006.01)
*A61K 8/97* (2006.01)
*A61K 9/00* (2006.01)
*A61K 36/89* (2006.01)

(52) U.S. Cl. ............ 424/725; 424/750; 424/778; 424/74

(58) Field of Classification Search .................. None
See application file for complete search history.

(56) References Cited

U.S. PATENT DOCUMENTS

| | | | |
|---|---|---|---|
| 2,559,459 A | 7/1951 | Peebles et al. | |
| 3,684,520 A | 8/1972 | Bickoff et al. | |
| 3,775,133 A | 11/1973 | Batley, Jr. et al. | |
| 3,799,806 A | 3/1974 | Madsen | |
| 3,821,346 A | 6/1974 | Batley, Jr. | |
| 3,823,128 A | 7/1974 | Bickoff et al. | |
| 3,849,391 A | 11/1974 | Egger et al. | |
| 3,957,774 A | 5/1976 | Kalopissis et al. | |
| 3,959,246 A | 5/1976 | Bickoff et al. | |
| 3,993,794 A | 11/1976 | Bernardin | |
| 4,006,078 A | 2/1977 | Bickoff et al. | |
| 4,066,633 A | 1/1978 | Gastineau et al. | |
| 4,072,666 A | 2/1978 | Horisberger et al. | |
| 4,077,950 A | 3/1978 | White | |
| 4,130,553 A | 12/1978 | Batley, Jr. | |
| 4,178,372 A | 12/1979 | Coats | |
| 4,208,323 A | 6/1980 | Murray et al. | |
| 4,233,210 A | 11/1980 | Koch | |
| 4,234,620 A | 11/1980 | Howard et al. | |
| 4,250,197 A | 2/1981 | Koch | |
| 4,333,871 A | 6/1982 | De Jong | |
| 4,334,024 A | 6/1982 | Johal | |
| 4,347,324 A | 8/1982 | Wildman et al. | |
| 4,359,530 A | 11/1982 | Brown | |
| 4,421,682 A | 12/1983 | Edwards et al. | |
| 4,551,341 A | 11/1985 | Blanie et al. | |
| 4,559,230 A | 12/1985 | David et al. | |
| 4,588,691 A | 5/1986 | Johal | |
| 5,043,427 A | 8/1991 | Leberre et al. | |
| 5,096,719 A | 3/1992 | Gresch | |
| 5,433,968 A | 7/1995 | Zarraga et al. | |
| 5,530,103 A | 6/1996 | Livey et al. | |
| 5,616,357 A | 4/1997 | Hartmann | |
| 5,723,149 A | 3/1998 | Bonte et al. | |
| 5,762,994 A | 6/1998 | Juillerat et al. | |
| 5,777,080 A | 7/1998 | Boatright | |
| 5,798,446 A | 8/1998 | Neumuller | |
| 5,882,664 A | 3/1999 | Soma et al. | |
| 5,932,233 A | 8/1999 | Yamamoto et al. | |
| 5,994,508 A | 11/1999 | Bryan et al. | |
| 6,013,771 A | 1/2000 | Shen et al. | |
| 6,037,456 A | 3/2000 | Garger et al. | |
| 6,060,061 A | 5/2000 | Breton | |
| 6,107,468 A | 8/2000 | Boatright | |
| 6,123,973 A | 9/2000 | Kuhn | |
| 6,139,825 A | 10/2000 | Reinhard et al. | |
| 6,147,054 A | 11/2000 | De Paoli Ambrosi | |
| 6,436,417 B1 | 8/2002 | Singh et al. | |

FOREIGN PATENT DOCUMENTS

| | | |
|---|---|---|
| GB | 2054343 A | 2/1981 |
| JP | 57-146715 | 9/1982 |
| JP | 05-229921 | 9/1993 |
| JP | 11-001686 | 1/1999 |

OTHER PUBLICATIONS

DW ACC 1995-083238, Feb. 1995, Derwent, Aeschbach et al.*
1995-083238, DW, Feb. 22, 1995, Aeschbach et al.
Hughes et al., "The Subcellular Distribution of Tocopherols in the Green Leaves of *Pisum sativum*," Biochem. J. 124 (2):9P-10P (1971).
Walk et al., "Purification and Characterization of Chloroplast Carbonate Dehydratase from Leaves of *Lactuca sativa*," Hoppe-Seyler's Z. Physiol. Chem. 356(11):1733-1741 (1975) (English Abstract).
Clifford et al., "Nucleic Acid Content and Nutritional Value of Green and White Leaf Proteins of Alfalfa," Nutr. Rep. Int. 15(5):511-518 (1977).
Lundborg, "Fractionation of Leaf Proteins by Differential Centrifugation and Gel Filtration," Physiol. Plant 48 (1):175-185 (1980).
Ostrowski-Meissner, "Quantities and Quality of Protein Extracted from Pasture Herbage Using Heat Precipitation or Ultrafiltration Procedures," J. Sci. Food Agric. 31:177-187 (1980).
Carroad et al., "Optimization of Cell Disruption for Alfalfa Leaf Protein Concentration (Pro-Xan) Production," J. Food Science 46:383-386 (1981).
Solinski, "The Precipitation of Protein Coagulates from Vegetable Juices," Pr. Nauk. Akad. Ekon. im. Oskara Langego Wroclawiu 199:91-123 (1982) (English Abstract).
Byers, "Extracted Leaf Proteins: Their Amino Acid Composition and Nutritional Quality," in Leaf Protein Concentrates 5:135-175 (Telek and Graham eds. 1983).

(Continued)

*Primary Examiner* — Christopher R Tate
*Assistant Examiner* — Randall Winston
(74) *Attorney, Agent, or Firm* — Heslin Rothenberg Farley & Mesiti P.C.; Andrew K. Gonsalves

(57) ABSTRACT

The present invention is directed to bioactive botanical cosmetic compositions derived from membrane and cell serum fractions of plant cell juice. The present invention also relates to the methods for preparing these bioactive botanical cosmetic compositions and the uses of these compositions in various cosmetic formulations and as topical skin cosmetic applications.

21 Claims, 1 Drawing Sheet

OTHER PUBLICATIONS

Koch, "The Vepex Process," in Leaf Protein Concentrates 22:601-632 (Telek and Graham eds. 1983).

Kohler et al., "LPC for Feeds and Foods: The Pro-Xan Process," in Leaf Protein Concentrates 18:508-524 (Telek and Graham eds. 1983).

Ostrowski-Meissner, "Protein Extraction from Grasslands," in Leaf Protein Concentrates 1:9-51 (Telek and Graham eds. 1983).

Ostrowski-Meissner, "Protein Concentrates from Pasture Herbage and Their Fractionation into Feed- and Food-Grade Products," in Leaf Protein Concentrates 15:437-466 (Telek and Graham eds. 1983).

Woodham, "The Nutritional Evaluation of Leaf Protein Concentrates," in Leaf Protein Concentrates 14:415-433 (Telek and Graham eds. 1983).

Bray, "Green Crop Fractionation: Product Improvement by Juice Purification," in Progress in Leaf Protein Research pp. 129-142 (1984).

Reddy et al., "Green Crop Fractionation: The Distribution of Crop Nutrients in Fractionation Products," Acta Botanica Indica 16(1):51-56 (1988).

Hanczakowski et al., "Composition and Nutritive Value of Native and Modified Green Fraction of Leaf Protein Lucerne (*Medicago sativa*)," J. Science Food and Agriculture 56(4):495-501 (1991).

Jwanny et al., "Protein Production for Human Use From Sugarbeet:Byproducts," Bioresource Tech. 43:67-70 (1993).

He et al., "The Comparison on Extraction Methods of Leaf Protein," J. Plant Resources and Environment 8(2):63-64 (1999).

* cited by examiner

BIOACTIVE BOTANICAL COSMETIC COMPOSITIONS AND PROCESSES FOR THEIR PRODUCTION

This application is a divisional of U.S. patent application Ser. No. 10/351,910, filed Jan. 24, 2003, which claims the priority benefit of U.S. Provisional Patent Application Ser. No. 60/351,886, filed Jan. 25, 2002, which are hereby incorporated by reference in their entirety.

FIELD OF THE INVENTION

The present invention relates to bioactive botanical cosmetic compositions and processes for their production and their use.

BACKGROUND OF THE INVENTION

Over the past several decades, the cosmetic industry has embraced the use of plants and plant products in a variety of cosmetic formulations and products. Although this trend is expected to continue, there is a need for more refined and higher quality botanical ingredients that consistently exhibit characteristics that are appealing to the cosmetic industry and consumers. Some of these appealing bioactive characteristics include anti-inflammatory and antioxidant activity. Coloration, safety, compatibility, and increased shelf life are also valuable characteristics of cosmetic formulations derived from botanical ingredients.

The cosmetic industry as a whole has increased its support of efforts to develop and market "natural" cosmetic formulations using a host of single and blended botanical ingredients that are currently available to the industry. This approach differs from the synthetic ingredient-based approach that has allowed the cosmetic industry to develop cosmetics with consistent product integrity, performance, and shelf life of raw material ingredients. One of the major deterrents toward the use of botanical ingredients is the inconsistency of the performance and stability of the ingredients, especially with regard to bioactive botanical ingredients. Many of the bioactive botanical cosmetic ingredients now used as ingredients in cosmetic formulations exhibit lost potency, odor deviations, unwanted darkening in coloration, and undesirable sedimentation. These negative attributes increase the risk of microbiological contamination and proliferation, instability, and safety concerns with regard to the final products made from the bioactive botanical ingredients.

In order to ensure quality, safety, and consistency, the cosmetic industry has developed and implemented various standard operating procedures and strict specification controls for all incoming raw materials for use in cosmetic formulations. Most, if not all, of the current botanical extracts fail to comply with the increasing controls and consistency parameters of the cosmetic industry. Current plant extraction methods limit product specification parameters leaving many windows of variability for quality, performance, and compatibility. In addition, current extraction methods fail to deliver the full spectrum of activities that exist within plant cells. Thus, the full potential of botanical-based cosmetic formulations is not being realized due to the inadequacy of the extraction methods for bioactive botanical cosmetic ingredients.

Many of the current methods for extracting bioactive components from plants involve techniques that are harmful to the plant tissue or the bioactive components of interest contained in that tissue, or both. Further, many of the current extraction and separation methods yield crude botanical extracts that contain biological or chemical contaminants that can cause a loss of bioactivity potency, increased cytotoxicity, and decreased shelf life. Further, in order to yield more refined botanical extracts, current extraction methods often require the use of harsh chemical solvents.

Thus, there is a need for a method of extracting bioactive botanical compositions that preserves the bioactivity of the composition and that yield consistent results from lot-to-lot. Further, botanical compositions that are able to meet the industry standards with respect to shelf life, cytotoxicity, quality, and performance are needed in the cosmetic industry.

The present invention is directed to overcoming these deficiencies in the art.

SUMMARY OF THE INVENTION

The present invention relates to a bioactive botanical cosmetic composition including (1) a membrane fraction derived from cell juice extracted from a fresh plant biomass and (2) a stabilizing agent. The membrane fraction has antiproteolytic activity, cell growth inhibition activity, and/or both antiproteolytic and cell growth inhibition activities. The antiproteolytic activity is due to inhibition of at least one proteinase and the cell growth inhibition activity is due to inhibition of proliferation of at least one type of cell.

The present invention also relates to a bioactive botanical cosmetic formulation suitable for topical application to a mammal. The bioactive botanical cosmetic formulation includes a cosmetically acceptable carrier and a cosmetically effective amount of the bioactive botanical cosmetic composition described above.

The present invention also relates to a method for inhibiting anti-inflammatory activity in skin tissue of a mammal. This method involves applying to the skin tissue the above described bioactive botanical cosmetic composition in an amount effective to enhance the antiproteolytic activity in the skin tissue.

The present invention also relates to a method for normalization of cell disorders in skin tissue of a mammal. This method involves applying to the skin tissue the above-described bioactive botanical cosmetic composition in an amount effective to inhibit unwanted hyper-proliferation of skin cells.

The present invention also relates to a method for preparing a bioactive botanical cosmetic composition, which involves providing a plant cell juice that has been extracted from a fresh plant biomass. The plant cell juice is then treated under conditions effective to separate it into a membrane fraction and a cell juice supernatant. The membrane fraction is transformed under conditions effective to yield a stable bioactive botanical cosmetic composition exhibiting antiproteolytic, cell growth inhibition activity, and/or both antiproteolytic and cell growth inhibition activities, where the antiproteolytic activity is due to inhibition of at least one proteinase and the cell growth inhibition activity is due to inhibition of cell growth of at least one type of cell.

The present invention also relates to a bioactive botanical cosmetic composition made by the method described immediately above.

The present invention also relates to a bioactive botanical cosmetic formulation suitable for topical application to a mammal. The formulation includes a cosmetically acceptable carrier and a cosmetically effective amount of the bioactive botanical cosmetic composition described immediately above.

The present invention also relates to a method for inhibiting anti-inflammatory activity in skin tissue of a mammal by applying to the skin tissue the bioactive botanical cosmetic composition described above in an amount effective to enhance the antiproteolytic activity in the skin tissue.

The present invention further relates to a method for normalization of cell disorders in skin tissue of a mammal, involving applying to the skin tissue the bioactive botanical cosmetic composition having cell growth inhibition activity in an amount effective to inhibit unwanted hyper-proliferation of skin cells.

The present invention also relates to a bioactive botanical cosmetic composition including the membrane fraction made by the method described above.

The present invention also relates to a bioactive botanical cosmetic composition including (1) a cell serum fraction derived from cell juice extracted from a fresh plant biomass, where the cell serum fraction has antioxidant activity, cell growth stimulation activity, and/or both antioxidant and cell growth stimulation activities, and (2) a stabilizing agent. The cell growth stimulation activity is due to stimulation of proliferation of at least one type of cell.

The present invention also relates to a bioactive botanical cosmetic formulation suitable for topical application to a mammal, including a cosmetically acceptable carrier and a cosmetically effective amount of the bioactive botanical cosmetic composition described immediately above.

The present invention further relates to a method for enhancing the antioxidant activity in skin tissue of a mammal, involving applying to the skin tissue of the mammal the bioactive botanical cosmetic formulation described above in an amount effective to increase the antioxidant activity in the skin tissue.

The present invention also relates to a method for stimulation of cell proliferation in skin tissue of the mammal, involving applying to the skin tissue the bioactive botanical cosmetic formulation described above in an amount effective to stimulate fibroblast proliferation in the skin tissue.

The present invention also relates to a method for preparing a bioactive botanical cosmetic composition, which involves providing a plant cell juice that has been extracted from a fresh plant biomass. The plant cell juice is then treated under conditions effective to separate the plant cell juice into a membrane fraction and a cell juice supernatant. The cell juice supernatant is processed under conditions effective to separate the cell juice supernatant into a cytoplasm fraction and a cell serum fraction. The cell serum fraction is refined under conditions effective to yield a cell serum fraction filtrate. The cell serum fraction filtrate is stabilized under conditions effective to yield a stable bioactive botanical cosmetic composition exhibiting antioxidant activity, cell growth stimulation activity, or both antioxidant and cell growth stimulation activities.

The present invention also relates to a stable bioactive botanical cosmetic composition made by the method described immediately above.

The present invention also relates to a bioactive botanical cosmetic formulation suitable for topical application to a mammal, including a cosmetically acceptable carrier and a cosmetically effective amount of the bioactive botanical cosmetic composition made by the process described above.

The present invention also relates to a method for enhancing the antioxidant activity in skin tissue of a mammal. This method involves applying to the skin tissue the bioactive botanical cosmetic composition described above in an amount effective to increase the antioxidant activity in the skin tissue.

The present invention further relates to a method of stimulation of cell proliferation in skin tissue of a mammal. This method involves applying to the skin tissue the bioactive botanical cosmetic composition described above in an amount effective to stimulate fibroblast proliferation in the skin tissue.

The method for preparing bioactive botanical cosmetic compositions is advantageous over the methods currently available in that it yields plant extracts that capture the full spectrum of activity contained in the plant cells. These extracts can then be separated into either cell serum or membrane components, while still maintaining the bioactivity contained within each component. Further, the compositions produced according to the method of the present invention have cytotoxicity profiles that are demonstrably safer for skin than other conventional plant extracts. In addition, the compositions of the present invention meet the microbial requirements of the cosmetic industry. Thus, due to the consistency, quality, safety, shelf life, and significant bioactivity potency with regard to anti-inflammatory and antioxidant capabilities, the bioactive botanical cosmetic compositions of the present invention are significant improvements over the botanical cosmetic ingredients available currently.

The bioactive botanical cosmetic compositions of the present invention exhibit the anti-inflammatory and antioxidant activities that are valuable to the cosmetic industry. Further, the cytotoxicity profiles of the bioactive botanical cosmetic compositions are within the industry standards for cosmetic ingredients and exhibit cell proliferative stimulatory activity and certain cell growth inhibitory activity at levels that are advantageous as topical skin cosmetics. The method for preparing the bioactive botanical cosmetic ingredients of the present invention may be used on a wide variety of plants to yield consistent, stable, and quality bioactive botanical cosmetic compositions.

The bioactive botanical cosmetic compositions of the present invention meet the industry standards with respect to the microbial requirements of cosmetic raw material ingredients. The industry standard requires that all active and inactive ingredients (i.e., all excipients of the cosmetic formulations) not be such that they contribute to the finished formulation composition of a cosmetic product. Typically, these finished formulation compositions have preservative systems that prevent microbial contamination that could risk the integrity of the product. In one standard use by the industry to test the protective strength of a preservative system, a product is subjected to a 28-day challenge test during which time microorganisms are inoculated into a product to see if it withstands these treatments without becoming contaminated. In addition, in the cosmetic industry, each ingredient is also scrutinized to make sure that the level of microorganisms is not so high as to result in subsequent contamination of a product or pose a risk on the shelf life of the product if it is not optimally preserved.

Specifically, the industry standard statistic that "the microbiological requirements for active ingredients in the cosmetic area state that a total microbial count of a maximum 100 microorganisms per gram or per ml may be tolerated. The sample (10 g) must furthermore be free from *Escherichia coli, Candida albicans, Pseudomonas* sp., and *Staphylococcus aureus*" (G. A. Nowak, "Cosmetic Preparations," *Verlag fur Chem.*, Augsburg, 1:126 (1985), the entire disclosure of which is incorporated herein by reference). The bioactive botanical cosmetic compositions of the present invention satisfy the above requirements and therefore pose no risk to finished cosmetic formulation compositions.

The bioactive botanical cosmetic compositions of the present invention have highly valuable bioactive attributes with respect to the skin, including, for example, anti-inflammatory and antioxidant activities, as well as cell proliferative stimulatory characteristics. It is generally known that there is the balance between newly born and dead skin cells. Optimum attributes of skin are found in young and healthy skin (i.e., usually found in people under the age of 25). Before this age, skin cells are in a regulated state and are in a well-balanced system of renewal; born at the deepest basal layers and eventually proliferating (i.e., rising from the deep skin) to the top (i.e., the layer which we visually appreciate). This balance of cells being shed is part of an equilibrium of renewal. This equilibrium is lost as a result of adult aging, and there is a slow down in the proliferation rate after new cells are born. The concept of increasing or stimulating cell proliferation is based on restoring the optimum equilibrium that is found in "younger" skin. This has led to an interest in cell proliferation stimulators such as retinoids and AHA (alpha hydroxy acids). Such ingredients basically increase the rate of proliferation through an irritation mode of action, leading to smoother, younger-looking skin due to accelerated cell proliferation. The bioactive botanical cosmetic compositions of the present invention, in particular those derived from the cell serum fractions, exhibit ability to stimulate cell proliferation.

In a more comprehensive manner, increased skin proliferation is a key to wound healing and dermatological conditions. There are certain dermatological conditions whereby skin proliferation tends to be in a hyper-proliferative state. These conditions border and cross disease states manifesting themselves on the skin. Conditions such as psoriasis, eczema, and dandruff are all hyper-proliferative conditions. Skin cell growth inhibitors are then the obvious and suggested approach to slowing down the rate of proliferation to normalize the rate. Various of the bioactive botanical cosmetic compositions of the present invention, in particular those derived from the membrane fraction, exhibit such cell inhibition attributes.

Inflammation occurs for many reasons on the skin. Usually associated with injury, today experts are beginning to understand the cascading effects of micro-inflammation. This micro-inflammation of the skin can result from irritating ingredients such as soaps and cytotoxic ingredients, ordinary UV light such as minimal sunlight, and in a more drastic manner from intense exposure to the sun. Recently, the role of inflammation on skin aging has been more clearly understood and suggested to be an indirect route to formation of free-radicals, which have been clearly implicated for their role in membrane lipid oxidation. Thus, anti-inflammatory agents are important cosmetic ingredients, but the regulatory restrictions limit their use as drugs. However, the bioactive botanical cosmetic compositions of the present invention, particularly those derived from the membrane fraction, demonstrate anti-inflammatory attributes.

The role of antioxidants has become increasingly important for nutrition and cosmetic products. Antioxidants retard, protect against, and help repair the adverse effects of oxidative degradation. In the plant world, nature has provided natural antioxidants that protect against many oxidative factors. The bioactive botanical cosmetic compositions of the present invention, particularly those derived from the cell serum fraction, demonstrate such antioxidant activity.

DETAILED DESCRIPTION OF THE INVENTION

Figure 1:
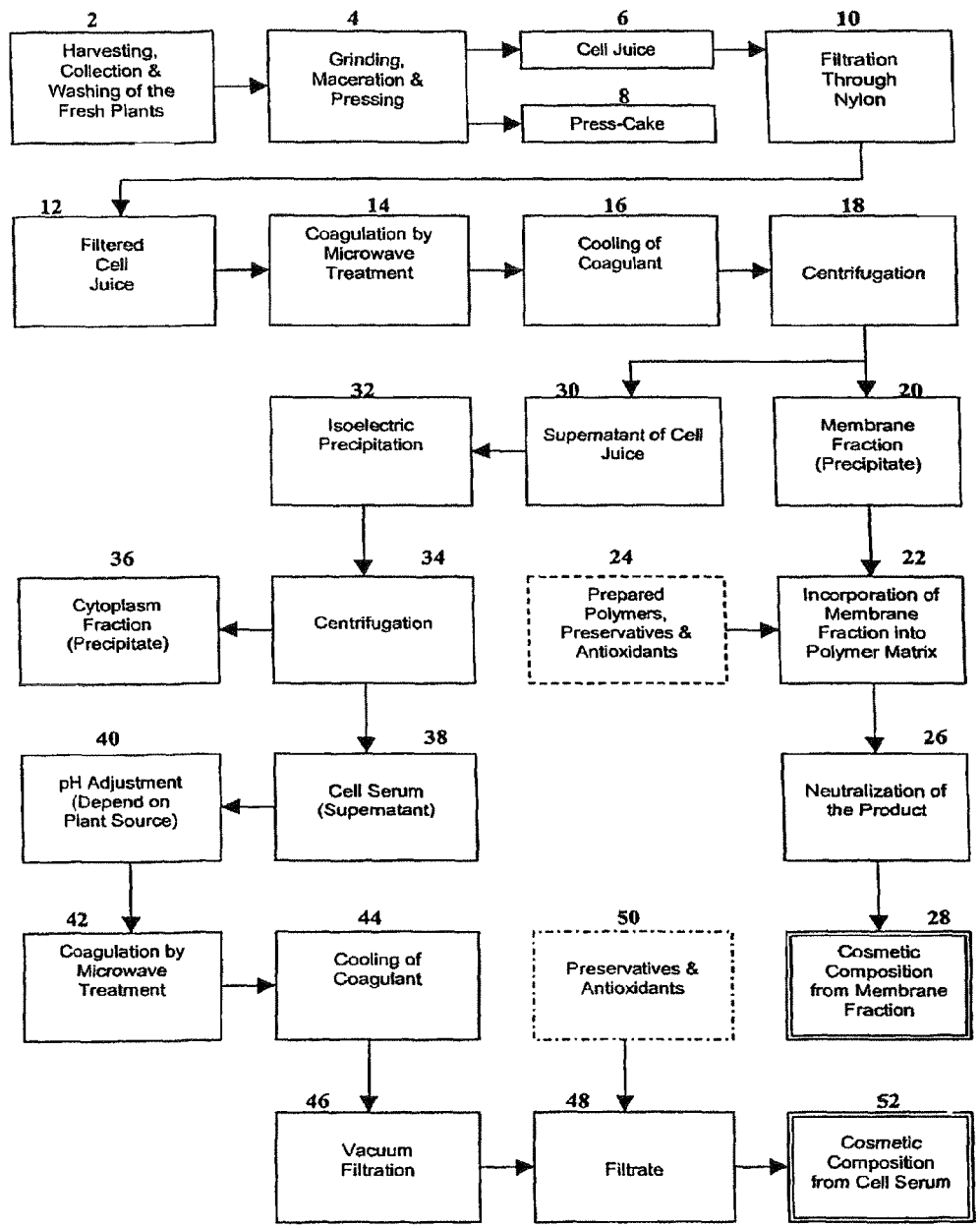
FIG. 1 is a schematic drawing demonstrating one embodiment of the process for preparing the bioactive botanical cosmetic compositions of the present invention.

The present invention relates to bioactive botanical cosmetic compositions derived from either the membrane fraction or the cell serum fraction of plants. As used herein, the term "Membrane-Derived Cosmetic Composition" generally refers to a bioactive botanical cosmetic composition of the present invention that is derived from the membrane fraction of a plant. The term "Serum-Derived Cosmetic Composition" generally refers to a bioactive botanical cosmetic composition of the present invention that is derived from the cell serum fraction of a plant.

The present invention also relates to processes for producing the bioactive botanical cosmetic compositions of the present invention, as well as methods for using the compositions.

Membrane-Derived Cosmetic Compositions

The Membrane-Derived Cosmetic Compositions of the present invention include (1) a membrane fraction derived from cell juice extracted from a fresh plant biomass and (2) a stabilizing agent. The membrane fraction has antiproteolytic activity, cell growth inhibition activity, and/or both antiproteolytic and cell growth inhibition activities. The antiproteolytic activity is due to inhibition of at least one proteinase and the cell growth inhibition activity is due to inhibition of proliferation of at least one type of cell. Examples of stabilizing agents that are suitable for use in the present invention include emulsifiers, preservatives, antioxidants, polymers, and mixtures thereof.

In one aspect of the present invention, the Membrane-Derived Cosmetic Composition has antiproteolytic activity against proteinase groups such as serine proteinases and matrix metalloproteinases. Examples of the serine proteinase include neutrophil elastase and trypsin inhibitor. An example of a matrix metalloproteinase is gelatinase B. In another aspect of the present invention, the inhibition of the proteinase is reversible. Since serine proteinases have certain positive physiological roles when present at controlled levels, use of reversible inhibitors will not impact these normal enzymatic functions. The reversible inhibition would not cause undesirable long term modifications to defense and repair mechanisms which can be impacted by irreversible inhibitors.

The Membrane-Derived Cosmetic Composition of the present invention has an antiproteolytic potency ranging from an $IC_{50}$ value of between about 0.1 and about 25.0 µg dry matter/ml. As used in the present application, the term "$IC_{50}$ value" represents the concentration of dry matter contained in the membrane fraction required to achieve 50 percent inhibition of the proteinase.

The Membrane-Derived Cosmetic Composition of the present invention has a cell growth inhibition activity potency ranging from an $NRU_{50}$ value of between about 25 and 500 µg dry matter/ml. As used in the present application, the term "$NRU_{50}$ value" represents the concentration of dry matter in the membrane fraction required to reduce the viability of the type of cell to 50 percent. An example of a type of cell that is inhibited from proliferating due to the Membrane-Derived Cosmetic Composition is a fibroblast.

The Membrane-Derived Cosmetic Composition of the present invention may be derived from membrane fractions of all types of plants. Examples of suitable plants that may be used as sources of fresh plant biomass in the present invention include plants from the following families: Asteraceae, Fabaceae, Lamiaceae, and Poaceae. In particular, examples of specific plants that have been tested and found appropriate as fresh plant biomass sources include *Calendula officinalis, Medicago sativa, Lavandula angustifolia, Salvia officinalis,* and *Hordeum vulgare.* The Membrane-Derived Cosmetic Composition may be derived from flower tissue (e.g., *Calendula officinalis*) and/or from leaf and stem tissue (e.g., *Salvia officinalis*) of plants.

In one embodiment, the membrane fraction derived from the plant cell juice makes up between about 0.5 and about 95 weight percent of the Membrane-Derived Cosmetic Composition.

The Membrane-Derived Cosmetic Composition of the present invention can have the following specific physicochemical values: (1) a non-volatile residue value of between about 0.1 and 30 percent; (2) a specific gravity value of between about 0.5 and 2.0 g/cm$^3$; (3) a viscosity value of between about 300 and 50,000 cps; and (4) a pH value of between about 2.5 and 9.5.

The present invention also relates to a bioactive botanical cosmetic formulation suitable for topical application to a mammal, including to humans, where the formulation includes a cosmetically acceptable carrier and a cosmetically effective amount of the Membrane-Derived Cosmetic Composition. Examples of suitable cosmetically acceptable carriers for use in the present invention include a hydrophilic cream base, a hydrophilic lotion base, a hydrophilic surfactant base, a hydrophobic cream base, a hydrophobic lotion base, and a hydrophobic surfactant base. In one embodiment of the formulation, the Membrane-Derived Cosmetic Composition is present in an amount ranging from between about 0.001 percent and about 90 percent of the total weight of the formulation.

The present invention also relates to a method for inhibiting anti-inflammatory activity in skin tissue of a mammal, which method involves applying to the skin tissue the Membrane-Derived Cosmetic Composition in an amount effective to enhance the antiproteolytic activity in the skin tissue.

The present invention also relates to a method for normalization of cell disorders in skin tissue of a mammal. This method involves applying to the skin tissue the Membrane-Derived Cosmetic Composition in an amount effective to inhibit unwanted hyper-proliferation of skin cells.

Serum-Derived Cosmetic Compositions

The Serum-Derived Cosmetic Compositions of the present invention include (1) a cell serum fraction derived from cell juice extracted from a fresh plant biomass, where the cell serum fraction has antioxidant activity, cell growth stimulation activity, and/or both antioxidant and cell growth stimulation activities, and (2) a stabilizing agent. The cell growth stimulation activity is due to stimulation of proliferation of at least one type of cell. Examples of stabilizing agents suitable for use in the present invention include a preservative and an antioxidant. Suitable preservatives for use in the present invention include potassium sorbate, sodium benzoate, sodium methyl paraben, and citric acid. An example of a suitable antioxidant for use in the present invention is sodium metabisulfite.

In one embodiment, the antioxidant activity of the Serum-Derived Cosmetic Composition includes superoxide scavenging activity and neutrophil respiratory burst inhibitory activity. The Serum-Derived Cosmetic Composition has a superoxide scavenging potency ranging from an $ICR_{50}$ value of between about 50 and 190 μg of dry matter/ml. As used in the present application, the term "$ICR_{50}$ value" represents the concentration of dry matter contained in the cell serum fraction required to inhibit 50 percent of cytochrome c reduction. The cell serum-derived cosmetic ingredient has a cell growth stimulation potency ranging from between about 1.0 and 125 μg of dry matter/ml and an NRU value of between about 110 and 190 percent, where the "NRU value" represents cell viability. The Serum-Derived Cosmetic Composition inhibits the respiratory bursts at between about 1.0 and 5.0 μg dry material/ml and stimulates the respiratory bursts at between about 120 and 180 μg dry material/ml. The Serum-Derived Cosmetic Composition has the ability to cause biphasic modulation of respiratory bursts from phorbol myristate acetate-stimulated neutrophils.

An example of a type of cell that is stimulated to proliferate due to the Serum-Derived Cosmetic Composition includes a fibroblast.

The Serum-Derived Cosmetic Composition of the present invention may be derived from cell serum fractions from all types of plants. Examples of suitable plants that may be used as sources of fresh plant biomass in the present invention include plants from the following families: Asteraceae, Fabaceae, Lamiaceae, and Poaceae. In particular, examples of specific plants that have been tested and found appropriate as fresh plant biomass sources include *Calendula officinalis, Medicago sativa, Lavandula angustifolia, Salvia officinalis*, and *Hordeum vulgare*. The Serum-Derived Cosmetic Composition may be derived from flower tissue (e.g., *Calendula officinalis*) and/or from leaf and stem tissue (e.g., *Horedeum vulgare, Lavandula angustifolia, Medicago sativa*, and *Salvia officinalis*).

In one embodiment, the cell serum fraction derived from the plant cell juice makes up between about 1 and 10 weight percent of the Serum-Derived Cosmetic Composition.

The present invention also relates to a bioactive botanical cosmetic formulation suitable for topical application to a mammal, including a cosmetically acceptable carrier and a cosmetically effective amount of the Serum-Derived Cosmetic Composition. Examples of suitable cosmetically acceptable carriers include, without limitation, a hydrophilic cream base, a hydrophilic lotion base, a hydrophilic surfactant base, a hydrophobic cream base, a hydrophobic lotion base, and a hydrophobic surfactant base. In one embodiment, the Serum-Derived Cosmetic Composition is present in an amount ranging from between about 0.001 percent and 95 percent of the total weight of the cosmetic formulation.

The present invention further relates to a method for enhancing the antioxidant activity in skin tissue of a mammal, involving applying to the skin tissue the Serum-Derived Cosmetic Composition in an amount effective to increase the antioxidant activity in the skin tissue.

The present invention also relates to a method for stimulation of cell proliferation in skin tissue of a mammal, involving applying to the skin tissue the Serum-Derived Cosmetic Composition in an amount effective to stimulate cell proliferation in the skin tissue.

Overall Process for Preparing Bioactive Botanical Cosmetic Compositions

By way of example, the overall process for preparing the bioactive botanical cosmetic compositions of the present invention is described below in reference to FIG. 1. As depicted in FIG. 1, fresh plants are harvested, collected, and washed 2 to yield fresh plant biomass. This fresh plant biomass is subjected to grinding, maceration, and pressing 4 to yield plant cell juice 6 and press-cake 8. Plant cell juice 6 is then filtered through nylon mesh 10 to yield filtered plant cell juice 12. Filtered plant cell juice 12 is exposed to microwave treatment 14 in order to coagulate plant cell juice 12. The coagulated plant cell juice is cooled 16 and then subjected to centrifugation 18 in order to yield membrane fraction 20 and plant cell juice supernatant 30. Membrane fraction 20 is used to prepare membrane-derived bioactive botanical cosmetic composition 28 (i.e., the Membrane-Derived Cosmetic Composition), as described below. Plant cell juice supernatant 30 is used to prepare cell serum-derived bioactive botanical cosmetic composition 52 (i.e., the Serum-Derived Cosmetic Composition), as described below.

To produce bioactive botanical cosmetic composition 28, membrane fraction 20 is incorporated into polymer matrix 22 and stabilized with prepared polymers, preservatives, and antioxidants 24. The stabilized membrane fraction is then neutralized 26 to yield the membrane-derived bioactive botanical cosmetic composition 28.

To produce bioactive botanical cosmetic composition 52, plant cell juice supernatant 30 is subjected to isoelectric precipitation 32 to yield a mixture containing cytoplasm fraction 36 and cell serum fraction 38. In order to separate cell serum fraction 38 from cytoplasm fraction 36, the mixture is subjected to centrifugation 34. Cell serum fraction 38 is then subjected to microwave treatment to cause coagulation 42. Depending on the plant source, prior to microwave treatment, cell serum fraction 38 is first pH-adjusted. After coagulation 42, the mixture is then cooled 44, followed by filtration 46 to yield cell serum filtrate 48. Cell serum filtrate 48 is stabilized with preservatives and antioxidants 50 to yield cell serum-derived bioactive botanical cosmetic composition 52.

Process for Preparing the Membrane-Derived Cosmetic Compositions

In one embodiment, the process for preparing the Membrane-Derived Cosmetic Compositions is as follows. This method involves providing plant cell juice that has been extracted from a fresh plant biomass. The plant cell juice is then treated under conditions effective to separate it into a membrane fraction and a cell juice supernatant. The resulting membrane fraction has antiproteolytic activity, cell growth inhibition activity, or both antiproteolytic and cell growth inhibition activities. The membrane fraction is then converted under conditions effective to yield a stable bioactive botanical cosmetic composition exhibiting antiproteolytic, cell growth inhibition activity, or both antiproteolytic and cell growth inhibition activities, where the antiproteolytic activity is due to inhibition of at least one proteinase and the cell growth inhibition activity is due to inhibition of cell growth of at least one type of cell.

The plant cell juice may be extracted from all types of plants. Examples of suitable plants that may be used as sources of fresh plant biomass in the present include, without limitation, plants from the following families: Asteraceae, Fabaceae, Lamiaceae, and Poaceae. In particular, examples of specific plants that have been tested and found appropriate as fresh plant biomass sources include *Calendula officinalis*, *Medicago sativa*, *Lavandula angustifolia*, *Salvia officinalis*, and *Hordeum vulgare*. Various parts of the plants may be used. For example, the stems and leaf tissue may be used for many types of plants. For other plants, the flowers may be used as sources of plant cell juice for use in the present invention. For example, one embodiment of the present invention uses flower tissue of *Calendula officinalis* for the extraction of the plant cell juice. In another embodiment, the leaf and stem tissue of *Salvia officinalis* is used.

The plant cell juice may be extracted using various extraction techniques. However, the extraction technique should result in plant cell juice that preserves the bioactive components of the plant.

An exemplary method of preparing the plant biomass for use in extraction of plant cell juice involves harvesting, collecting, and washing of the fresh plants. Suitable steps to follow for preparing the fresh plant biomass include, for example, the following: (1) preservation of the inherent moisture content of the plant cells; (2) optimization of the height of cut used during harvesting of above-ground plant tissue; (3) reservation of plant integrity during harvesting (e.g., during cutting of the above-ground plant tissue); (4) minimization of environmental impact and time factors of biological degradation of the plant biomass; and (5) cleaning of the plant biomass prior to processing (e.g., prior to grinding and maceration). Each of these steps is discussed below.

Preservation of Inherent Moisture Content: The cutting should be done to avoid wilting due to moisture loss. Optimal conditions are those where natural moisture content is maintained and preserved.

Optimal and Preferred Height of Cut: The plants should be cut at least several centimeters above the ground to limit the amount of soil and other debris in the collected biomass. For example, all useable leaf and stem biomass of any given plant source (e.g., alfalfa, barley, lavender, or sage) may be cut at a height of greater than or equal to 5 centimeters above ground. If flower tissue is used as the plant biomass source, the flowers are separated from the whole plant prior to extraction of the plant cell juice.

Preservation of Plant Integrity During Harvesting: Harvesting of the plant biomass may be by cutting the above ground stem and leaf tissue of the plant. The cutting is conducted in a manner that avoids or minimizes the chopping, mashing, crushing, or other type of injury of the plant. For large-scale industrial harvesting, where it may not be possible to avoid chopping due to the type of equipment required, care is taken to minimize injury that could lead to microbial growth, moisture loss, intensification of oxidation, polymerization, isomerization, and hydrolysis processes (i.e., unwanted catabolic processes) in collected plants. For example, in one embodiment of the present invention, lavender and sage are cut and collected by hand as whole plants. In another embodiment, alfalfa and barley tissue are cut using harvesting equipment. In that case, the minimum chopping height above ground for each plant is greater than or equal to 5 centimeters. Further, particular attention is made to minimize injury, during and after cutting. In another embodiment, marigold whole plants are collected by hand and the flowers are then separated for further processing.

Minimization of Environmental Impact and Time Factors of Degradation: Delivery time of cut plant material to the processing facility and exposure of biomass to sun, high temperature, and other negative environmental factors, should be minimized to prevent the impact of unwanted degradation processes as described above. For example, in one embodiment of the present invention, the delivery time for alfalfa and barley for further processing does not exceed 30 minutes from the time of cutting. In another embodiment, plants that undergo long distance transport are treated to a post-cutting procedure involving immediately placing the plant biomass into Styrofoam coolers containing bags of frozen gel packs to help maintain freshness and natural moisture content during overnight delivery to the processing facility. These procedures were conducted for plant biomass from lavender, marigold, and sage. Other post-cutting procedures that achieve the results described above may be used as well.

Cleaning Step Prior to Grinding and Maceration: A washing step to remove the soil particles and other debris from plants prior to further processing is performed once the plant tissue is harvested. The washing is achieved using a low-pressure rinse for a short duration under conditions to prevent the initiation of the release of the cell juice from biomass, to cause injury, or to remove valuable components. For example, in one embodiment of the present invention, the washing of the plant biomass was accomplished in less than or equal to 5 minutes with a water pressure of less than or equal to 1 kg/cm$^2$. Residual water wash did not contain any green or yellow pigments, which indicates the absence of subsequent injury. The excess water is removed from washed biomass in order to keep the dry matter content close to natural level.

After the plant tissue biomass is harvested, as described above, further processing of the plant tissue biomass is performed to yield plant cell juice. In one embodiment, the harvested plant tissue biomass is subjected to grinding, maceration, and pressing to extract the intracellular content, i.e., the cell juice, and to separate it from the fiber-enriched presscake containing predominantly cell walls.

An example of a suitable processing protocol involves the steps described below. A hammer mill may be used to grind plants to yield plant tissue particles of a small size in a short time and without significant increase of biomass temperature. In one embodiment, a modified hammer mill is used to produce the maximum size of macerated plant particles less than or equal to 0.5 centimeters during less than or equal to 10 seconds of treatment, where the increase of biomass temperature is less than or equal to 5° C.

Exposure of ground and macerated plant biomass is minimized to prevent the impact of unwanted catabolic processes, as described above. The extraction of the plant cell juice and its separation from the press-cake is commenced as soon as possible after grinding and maceration of the plant biomass. The plant biomass is processed in a short time and without significant increase in temperature. In one embodiment, immediately after grinding and maceration, the plant biomass is pressed using a horizontal, continuous screw press (Compact Press "CP-6", Vincent Corporation, FL). The pressure on the cone is maintained at level 24 kg/cm$^2$, screw speed is at 12 rpm, and the temperature increase is less than or equal to 5° C.

The initial cell juice usually contains small fiber particles, which can absorb valuable cell juice components and also block the hoses and pumps. The above particles should be removed by filtration or low-speed centrifugation. For example, the initial cell juices produced after the pressing step are filtered through four layers of nylon fabric prior to using the plant cell juice in the methods of the present invention.

Once plant cell juice is extracted, the plant cell juice is then treated to a processes involving (1) performing a "membrane fraction coagulation step" to yield a coagulated cell juice mixture and (2) performing a "membrane fraction separation step" on the coagulated cell juice mixture to yield a membrane fraction and a cell juice supernatant. In one embodiment, the membrane fraction coagulation step includes destabilizing the cell juice to yield a coagulated cell juice mixture. The destabilizing may be achieved using a variety of destabilization techniques, including, for example, temperature treatment, electro-membrane treatment, and chemical treatment. Suitable temperature treatment for use in the present invention may include (1) heating the cell juice extract to a treatment temperature required to induce coagulation of the membrane fraction (e.g., to a temperature of between about 45 and 70, degrees Celsius) and (2) cooling the cell juice to a temperature effective to allow further quantitative separation of said membrane fraction from said cell juice supernatant (e.g., to a temperature of between about 30 and 45 degrees Celsius). After destabilization is achieved, a membrane fraction separation step is performed. This step includes, for example, separating the coagulated cell juice mixture into the membrane fraction and the cell juice supernatant using separating techniques including filtration and centrifugation.

The freshly obtained membrane fraction commonly referred to in the art, as "protein-vitamin concentrate," is a paste having intensive color and specific odor that is plant raw material source specific. The membrane fraction is represented predominantly by chloroplasts present in the green parts of plant or mostly by chromoplasts present in flowers. The composition of the membrane fraction includes predominantly phospholipids, membrane proteins, chlorophyll, and carotenoids. The drying of membrane fraction results in irreversible loses of many valuable properties required for the exploration of membrane fraction as a cosmetic ingredient. Without drying, the unstable membrane fraction is quickly transformed into the dark color un-dispersible and insoluble conglomerates having strong and non-characteristic odor. As result, such material cannot be used as a cosmetic ingredient. The described procedure that follows allows for transformation of freshly obtained membrane fractions into stable and active cosmetic ingredients.

Once the membrane fraction is separated from the cell juice supernatant, the membrane fraction is then subjected to a formulation process prior to aggregation of the membrane fraction, including the following steps: (11) performing a "stabilization step" to yield a stabilized membrane fraction component; (2) performing a "polymer matrix incorporation step" on the stabilized membrane fraction component to yield a membrane fraction matrix; and (3) performing a "neutralization step" on the membrane fraction matrix to yield the Membrane-Derived Cosmetic Composition of the present invention.

In one embodiment, the stabilization step involves mixing a non-ionic emulsifier and at least one antioxidant with the membrane fraction to yield a stabilized membrane fraction component. In the polymer matrix incorporation step, the stabilized membrane fraction component is incorporated into a polymer matrix to yield a membrane fraction matrix. Suitable polymers for use in the present invention include, for example, at least one polymeric emulsifier and at least one preservative. The membrane fraction matrix is then subjected to the neutralization step, which step involves adjusting the pH of the membrane fraction matrix to a range of between 2.5 and 6.5, yielding the Membrane-Derived Cosmetic Composition described in the present application.

In another embodiment, stabilization of the Membrane-Derived Cosmetic Composition to yield approximately 100 grams of the composition is performed as follows:

(a) Stabilization of membrane fraction includes its mixing with non-ionic emulsifier Polysorbate 80 (Tween 80) and antioxidants (Tenox 4). As an example, 20 grams fresh membrane fraction are mixed vigorously until homogeneous with 3.5 grams of Tween 80 and 0.1 gram of Tenox 4 (solution of Butylated Hydroxyanisole and Butylated Hydroxytoluene in oil) while avoiding aeration during mixing.

(b) Preparation of the dispersion of polymeric emulsifier, acrylates/C10-C30 acrylate crosspolymer: As an example, 0.9 gram Pemulen TR-2 was dispersed in 69.2 grams warm deionized water and mixed until uniform using moderate agitation, avoiding aeration. In parallel, 5 grams of Glycerin and 1 gram of Phenonip (mixture of Phenoxyethanol (and) Methylparaben (and) Butylparaben (and) Ethylparaben (and) Propylparaben) are combined in separate vessel and mixed until uniform. With moderate agitation, phases containing Pemulen and Glycerin with Phenonip are combined and mixed until uniform.

(c) Incorporation of membrane fraction into polymer matrix: As an example, the phase containing membrane fraction, Tween 80 and Tenox 4 is added to the phase containing Pemulen, Glycerin and Phenonip and mixed with vigorous agitation while avoiding aeration.

(d) Neutralization of the product: As an example, the batch containing membrane fraction and other components is neutralized with 18% aqueous solution of Sodium Hydroxide (NaOH) and mixed vigorously to produce uniform system having pH=5.0±0.4.

The resulting multiphase products are opaque gels demonstrating properties that fully satisfy all requirements to the cosmetic ingredients. It was found that optimum composition of preservatives and anti-oxidants in multiphase cosmetic ingredients is very similar for all plant sources and different combinations of Pemulens and also Carbopols can be effectively used. Stability studies indicate that cosmetic ingredients produced from membrane fractions via methods described are stable at 8° C. for at least 4-6 months maintaining physico-chemical integrity and activities.

Process for Preparing Serum-Derived Cosmetic Compositions

The present invention also relates to a method for preparing the Serum-Derived Cosmetic Composition exhibiting antioxidant activity, cell growth stimulation activity, or both antioxidant and cell growth stimulation activities. The method involves providing a plant cell juice that has been extracted from a fresh plant biomass, as already described above with respect to the Membrane-Derived Cosmetic Composition. The plant cell juice is then treated under conditions effective to separate the plant cell juice into a membrane fraction and a cell juice supernatant. This step is also the same as described above with respect to the Membrane-Derived Cosmetic Composition. The cell juice supernatant is processed under conditions effective to separate the cell juice supernatant into a cytoplasm fraction and a cell serum fraction. The cell serum fraction is refined under conditions effective to yield a cell serum fraction filtrate having antioxidant activity, cell growth stimulation activity, or both antioxidant and cell growth stimulation activities. The cell serum fraction filtrate is stabilized under conditions effective to yield a stable bioactive botanical cosmetic composition exhibiting antioxidant activity, cell growth stimulation activity, or both antioxidant and cell growth stimulation activities.

The plant cell juice may be extracted from all types of plants. Examples of suitable plants that may be used as sources of fresh plant biomass in the present include, without limitation, plants from the following families: Asteraceae, Fabaceae, Lamiaceae, and Poaceae. In particular, examples of specific plants that have been tested and found appropriate as fresh plant biomass sources include *Calendula officinalis, Medicago sativa, Lavandula angustifolia, Salvia officinalis,* and *Hordeum vulgare.*

As described above, once the plant cell juice is separated into a membrane fraction and a cell juice supernatant, the cell juice supernatant is subjected to a processing step. In one embodiment, the processing step involves (1) performing a "cytoplasmic fraction precipitation step" to yield a cytoplasm/cell serum mixture including the cytoplasmic fraction and the cell serum fraction, and (2) performing a "cell serum separation step" to separate the cytoplasmic fraction from the cell serum fraction. The cytoplasmic fraction includes predominantly white soluble proteins; in C3 plants, these proteins largely consist of the enzyme ribulose biphosphate carboxilase. The cell serum contains low molecular weight soluble components.

The cytoplasmic fraction precipitation step may include inducing precipitation of the cytoplasmic fraction within the cell juice supernatant using a suitable precipitation technique, including, for example, isoelectric titration and electrodialysis. In one embodiment, the isoelectric titration involves adjusting the pH of the cell juice supernatant to between about 2.5 and 6.5. The cytoplasm/cell serum mixture is induced to separate into a cytoplasmic fraction and a cell serum fraction using a suitable separation technique, including, for example, such techniques as filtration and centrifugation. As an example, the precipitation was induced by a titration method utilizing by 5.0N Hydrochloric Acid (HCl) to pH=4.0.

The quantitative criteria to evaluate the complete separation of cytoplasm fraction is the absence of detectable levels of high molecular weight proteins and/or the absence of ribulose biphosphate carboxilase in subsequent filtrate or supernatant. As an example, the precipitated cell juice supernatants may be separated in a refrigerated centrifuge for greater than or equal to 20 minutes at greater than or equal to 3,000 g, and an absence of the proteins having molecular weight of greater than or equal to 10,000 in cell serum having pH=4.0 were achieved.

The cell serum is commonly referred to as "brown juice," although initially this clear liquid has a slight yellow color and slight characteristic odor. In several hours, the unstable cell serum is irreversibly transformed into dark brown color suspension containing heavy precipitate and strong non-characteristic odor. As a result, "brown juice" cannot be used as a cosmetic ingredient. The described procedure that follows allows for the refinement of cell serum (brown juice) to yield a stable and active cosmetic ingredients. This is accomplished by removing from the cell serum the major components responsible for the irreversible transformations that lead to generation of unwanted precipitate and deterioration of color and odor. This procedure includes: pH adjustment, heat treatment, cooling, vacuum filtration, and stabilization. Some specific regiment procedures may vary according to plant source cell serum. It should be noted that this procedure must be used immediately after separation of cell serum from cytoplasm fraction is completed.

Once the cell serum fraction is produced, it is the subjected to a refining process. This refining process includes (1) performing a "temperature treatment step" to yield a coagulated cell serum fraction, and (2) performing a clarification step to yield a cell serum fraction filtrate. A suitable temperature treatment step for use in the present invention involves (1) heating the cell serum fraction to a heating temperature required to induce coagulation within the cell serum fraction, and (2) immediately cooling the cell serum fraction to a temperature effective to allow further quantitative separation of said cell serum fraction filtrate. In one embodiment, the heating temperature is between about 80 and about 95 degrees Celsius, and the cooling of the heated cell serum fraction is to a temperature of at least as low as about 15 degrees Celsius. A suitable clarification step for use in the present invention involves clarifying the coagulated cell serum fraction to yield a cell serum fraction filtrate, where the clarifying involves clarification techniques such as filtration and centrifugation. In one embodiment, the filtration may involve vacuum filtrating the coagulated cell serum fraction to yield the cell serum fraction filtrate. In another embodiment, prior to the temperature treatment step, the cell serum fraction is adjusted to a pH of between about 3.0 and 4.0, as appropriate.

After the cell serum filtrate is produced, it is then subjected to the stabilizing step mentioned above to yield the Serum-Derived Cosmetic Composition. In one embodiment, the stabilizing step involves incubating the cell serum fraction filtrate in a mixture of at least one preservative and at least one antioxidant to yield a stabilized cell serum fraction filtrate. Suitable preservatives for use in the present invention include, for example, potassium sorbate, sodium benzoate, sodium methyl paraben, and citric acid. An example of a suitable antioxidant for use in the present invention is sodium metabisulfite.

In one embodiment, stabilization of the cell serum may be performed as follows:

(a) As an example, the pH adjustment is performed for cell serum obtained from sage and marigold flowers induced by a titration method utilizing by 5.0N Hydrochloric Acid (HCl) to pH=3.0. Such adjustment is not necessary for cell serum obtained from alfalfa, barley and lavender.

(b) Heat treatment is performed for cell sera obtained from all useable plant sources. As an example, cell sera are exposed to microwave treatment under the temperature probe control. This treatment is continued until the temperature reaches 90° C. The temperature probe indicates the point required to induce the complete coagulation of the unwanted components. Once coagulation is induced, the treated cell juice is immediately cooled to 10° C.

(c) The coagulated cell sera can be clarified by filtration or centrifugation. As an example, the coagulated cell sera may be vacuum filtrated through double layers of Whatman No. 2 filters. The precipitates are discarded, and filtrates are used for further processing.

(d) Stabilization of the filtrates included addition of specific preservatives and anti-oxidants and incubation of the mixtures until their complete solubilization is achieved (usually greater than or equal to 30 minutes of extensive mixing is required).

Stabilized cell serum filtrates demonstrate properties which fully satisfy all requirements of cosmetic ingredients. Stability studies indicate that cosmetic ingredients produced from cell serum via these methods are stable at room temperature for at least 10-12 months (i.e., they maintain physico-chemical integrity and activities).

EXAMPLES

Example 1

Preparation of Cosmetic Botanical Ingredient 101 Derived from Alfalfa (*Medicago sativa*) Cell Serum Fractions Biomass Preparation. Sufficient amounts of fresh alfalfa (*Medicago sativa*) plant biomass (i.e., stem and leaf tissue) were harvested to yield approximately 100 kg of dry matter. The level of dry matter in the fresh alfalfa plant biomass was calculated to be 15.75 percent, requiring harvesting of approximately 635 kg of fresh alfalfa plant biomass to yield 100 kg of dry matter. Care was taken to preserve the inherent moisture content of the plant biomass and to avoid wilting due to moisture loss. The plants were cut at least 5 centimeters above the ground to limit the amount of soil and other debris in the collected plant biomass. The cutting was conducted in such a manner as to avoid or minimize chopping, mashing, and crushing of the plants. The harvested plants were delivered for processing not more than 60 minutes after cutting. This was done to minimize exposure of the plant biomass to sun, high temperature, and other negative environmental factors. A washing step was performed to remove soil particles and other debris from the plants prior to further processing. This washing was accomplished by washing the harvested plants for $\leq 5$ minutes in $\leq 1$ kg/cm$^2$ water pressure. The residual water wash did not contain any green pigments, indicating proper water pressure and washing duration. The excess water was removed from the washed plant biomass.

Grinding, Maceration, and Pressing of Plant Biomass. After harvesting, collecting, and washing the plant biomass, the plants then underwent grinding, maceration, and pressing to extract the intracellular content (i.e., the plant cell juice) and to separate it from the fiber-enriched press-cake. A hammer mill was used to grind the alfalfa biomass to yield plant tissue particles of suitably small size in a short amount of time and without significant increase of biomass temperature. The hammer mill was set to produce the maximum size of macerated plant particles of $\leq 0.5$ centimeters during $\leq 10$ seconds of treatment. This resulted in only an increase of $\leq 5°$ C. biomass temperature. A horizontal continuous screw press (Compact Press "CP-6", Vincent Corporation, FL) was used to extract the plant cell juice from the plant biomass. The pressure on the cone of the screw press was maintained at a level of 24 kg/cm$^2$, with a screw speed of 12 rpm and only a temperature increase of $\leq 5°$ C. This treatment yielded the press-cake and the plant cell juice. The initial plant cell juice contained small fiber particles, which were removed by filtration through four layers of nylon fabric or by using low-speed centrifugation.

Separation of the Membrane Fraction from the Cell Juice. The filtered plant cell juice was exposed to microwave treatment using a temperature probe control. This treatment continued until the temperature of the cell juice reached 60° C. Once coagulation was induced, the treated cell juice was immediately cooled to 40° C. Separation of the membrane fraction from the coagulated cell juice was achieved using centrifugation at greater than or equal to 3,000 g for greater than or equal to 20 minutes. This yielded a membrane fraction (precipitate) and a cell juice supernatant, which contained a cytoplasm fraction and a cell serum fraction (i.e., low molecular weight soluble components). The cell juice supernatant was used for further processing to yield Cosmetic Botanical Ingredient 101. The membrane fraction was preserved for use in preparing a counterpart Membrane-Derived Cosmetic Composition.

Separation of the Cytoplasm Fraction from the Cell Juice Supernatant. In order to separate out the cytoplasm fraction, the cell juice supernatant was subjected to isoelectric precipitation. Precipitation of the cytoplasm fraction was induced using a titration method utilizing 5.0 N hydrochloric acid (HCl) to bring the pH of the cell juice supernatant to 4.0. The separation of precipitated cytoplasm fraction from the cell serum was achieved by centrifugation at greater than or equal to 3,000 g for greater than or equal to 20 minutes. This resulted in a cell serum (supernatant) that could be further refined to yield Botanical Cosmetic Ingredient 101.

Treatment of the Cell Serum to Produce Cosmetic Botanical Ingredient 101. The refinement of the cell serum involved the following steps: heat treatment, cooling, filtration, and stabilization. Refinement was performed immediately after separation of the cell serum from the cytoplasm fraction. The cell serum was exposed to microwave treatment using a temperature probe control. This treatment continued until the temperature of the cell serum reached 90° C. Once coagulation was induced, the treated cell serum was immediately cooled to 10° C. The coagulated cell serum was vacuum filtrated through double layers of Whatman No. 2 filters. The precipitate was discarded and the resulting cell serum filtrate was used for further processing (i.e., stabilization). Stabilization of the cell serum filtrate was achieved by adding preservatives and antioxidants and incubating the mixture until complete solubilization was achieved. The preservatives and antioxidants used included the following: 0.1% potassium sorbate, 0.1% sodium benzoate, 0.1% sodium methyl paraben, and 0.2% sodium metabisulfite. This preparation resulted in the production of 18.1 kg of Dry Matter yield (or approximately 340 Liters) of the Cosmetic Botanical Ingredient 101, which was used for characterization of its physico-chemical and bioactive qualities. The recommended storage conditions for Cosmetic Botanical Ingredient 101 include storage in a closed container protected from light at a temperature of between 15 and 25° C.

Example 2

Product Specifications of Cosmetic Botanical Ingredient 101 Derived from Alfalfa (*Medicago sativa*) Cell Serum Fractions Cosmetic Botanical Ingredient 101 was prepared according to the process described above in Example 1. Analyses of Cosmetic Botanical Ingredient 101 were conducted to determine its various physico-chemical, microbial, cytotoxicity, and bioactivity characteristics, as described below. Cosmetic Botanical Ingredient 101 is a clear liquid, which has a light-yellow color and a light-characteristic odor. No solvent (i.e. glycol, oil, or water) was added to the carrier medium.

Table 1 summarizes the Physical and Chemical data of Cosmetic Botanical Ingredient 101.

TABLE 1

Physical and Chemical Data

| Parameter | Method | Results |
|---|---|---|
| Solid Content, % | See Example 25, "Method 1" | 5.3 |
| Specific Gravity, g/cm$^3$ | USP <841> | 1.025 |
| Color | Gardner Scale | 6-7 |
| Refractive Index | USP <831> | 1.342 |
| pH | USP <791> | 4.1 |
| Red-Ox Potential, mV | See reference [1] | 70 |
| Conductivity, S/m | See reference [2] | 0.96 |

References:
[1] Handbook of Chemistry and Physics, 80$^{th}$ Edition, CRC Press, 1999-2000, 5-90;
[2] Handbook of Chemistry and Physics, 80$^{th}$ Edition, CRC Press, 1999-2000, 8-21, which are hereby incorporated by reference in their entirety.

Table 2 describes the UV-Spectra data regarding Cosmetic Botanical Ingredient 101.

TABLE 2

UV-Spectra

| Peak | Parameter | Method | Results |
|---|---|---|---|
| #1 | Start, nm | USP <197> | 400.0 |
|  | Apex, nm | " | 324.5 |
|  | End, nm | " | 303.0 |
|  | Height, Abs | " | 0.347 |
|  | Area, Abs × nm | " | 21.197 |
| #2 | Start, nm | USP <197> | 303.0 |
|  | Apex, nm | " | 258.0 |
|  | End, nm | " | 233.0 |
|  | Height, Abs | " | 1.471 |
|  | Area, Abs × nm | " | 65.103 |

Table 3 summarizes the microbial analysis data for Cosmetic Botanical Ingredient 101. This data demonstrates that Cosmetic Botanical Ingredient 101 satisfies the cosmetic industry requirements regarding colony forming units and absence of pathogens.

TABLE 3

Microbial Analysis

| Parameter | Method | Results |
|---|---|---|
| Colony Forming Units (CFU) per gram of sample | USP <61> | <100 |
| Escherichia coli | " | Negative |
| Candida albicans | " | Negative |
| Pseudomonas sp. | " | Negative |
| Staphylococcus aureus | " | Negative |

Cosmetic Botanical Ingredient 101 was determined to be stable (i.e., maintaining physical and chemical integrity) for at least 12-18 months while stored at a temperature of between 15 and 25° C. in a closed container protected from light. No toxic effect was detected. In a controlled clinical evaluation, Cosmetic Botanical Ingredient 101 did not demonstrate 50% inhibition of neutral red uptake ($NRU_{50}$) by 3T3 fibroblasts in the concentration range 0-2,500 μg dry matter/ml. The $NRU_{50}$ of positive control (epidermal growth factor) >2,500 μg/ml. Cosmetic Botanical Ingredient 101 demonstrated superoxide scavenging ability. In a controlled clinical evaluation, Cosmetic Botanical Ingredient 101 demonstrated a 50% inhibition of cytochrome c reduction ($ICR_{50}$) at a concentration 149 μg dry matter/ml. The $ICR_{50}$ of positive control (rosmarinic acid)=26.5 μg/ml. Cosmetic Botanical Ingredient 101 is a biodegradable product.

Example 3

Preparation of Cosmetic Botanical Ingredient 201 Derived from Barley (*Hordeum vulgare*) Cell Serum Fractions The process for preparing Cosmetic Botanical Ingredient 201 was identical to the process described in Example 1 with regard to Cosmetic Botanical Ingredient 101, with the variations noted below. Fresh stem and leaf tissue of barley (*Hordeum vulgare*) was used as the plant biomass starting material. The level of dry matter in the fresh barley plant biomass was calculated to be 13.67 percent, requiring harvesting of approximately 732 kg of fresh barley plant biomass to yield 100 kg of dry matter. The preparation resulted in the production of 15.1 kg of Dry Matter yield (or approximately 433 liters) of Cosmetic Botanical Ingredient 201.

Example 4

Product Specifications of Cosmetic Botanical Ingredient 201 Derived from Barley (*Hordeum vulgare*) Cell Serum Fractions Cosmetic Botanical Ingredient 201 was prepared according to the process described above in Example 3. Analyses of Cosmetic Botanical Ingredient 201 were conducted to determine its various physico-chemical, microbial, cytotoxicity, and bioactivity characteristics, as described below. Cosmetic Botanical Ingredient 201 is a clear liquid, which has a light-yellow color and a light-characteristic odor. No solvent (i.e., glycol, oil, or water) was added to the carrier medium.

Table 4 summarizes the Physical and Chemical data of Cosmetic Botanical Ingredient 201.

TABLE 4

Physical and Chemical Data

| Parameter | Method | Results |
|---|---|---|
| Solid Content, % | See Example 25, "Method 1" | 3.5 |
| Specific Gravity, g/cm$^3$ | USP <841> | 1.019 |
| Color | Gardner Scale | 5-6 |
| Refractive Index | USP <831> | 1.338 |
| pH | USP <791> | 4.1 |
| Red-Ox Potential, mV | See reference [1] | 95 |
| Conductivity, S/m | See reference [2] | 1.09 |

References:
[1] Handbook of Chemistry and Physics, 80$^{th}$ Edition, CRC Press, 1999-2000, 5-90;
[2] Handbook of Chemistry and Physics, 80$^{th}$ Edition, CRC Press, 1999-2000, 8-21, which are hereby incorporated by reference in their entirety.

Table 5 summarizes the UV-Spectra data for Cosmetic Botanical Ingredient 201.

TABLE 5

UV-Spectra

| Peak | Parameter | Method | Results |
|---|---|---|---|
| #1 | Start, nm | USP <197> | 400.0 |
|  | Apex, nm | " | 333.5 |
|  | End, nm | " | 305.0 |
|  | Height, Abs | " | 0.232 |
|  | Area, Abs × nm | " | 14.254 |
| #2 | Start, nm | USP <197> | 305.0 |
|  | Apex, nm | " | 258.0 |
|  | End, nm | " | 233.0 |
|  | Height, Abs | " | 1.268 |
|  | Area, Abs × nm | " | 55.631 |

Microbial analyses demonstrated that Cosmetic Botanical Ingredient 201 satisfies the cosmetic industry requirements for cosmetic ingredients with regard to CFUs and absence of pathogens (see Table 3, above, for methods).

Cosmetic Botanical Ingredient 201 was determined to be stable (i.e., maintaining physical and chemical integrity) for at least 12-18 months while stored at a temperature of between 15 and 25° C. in a closed container protected from light. No toxic effect was detected. In a controlled clinical evaluation, Cosmetic Botanical Ingredient 201 did not demonstrate 50% inhibition of neutral red uptake (NRU$_{50}$) by 3T3 fibroblasts in the concentration range 0-2,500 μg dry matter/ml. The NRU$_{50}$ of positive control (epidermal growth factor) >2,500 μg/ml. Cosmetic Botanical Ingredient 201 demonstrated superoxide scavenging ability. In a controlled clinical evaluation, Cosmetic Botanical Ingredient 201 demonstrated a 50% inhibition of cytochrome c reduction (ICR$_{50}$) at a concentration 160 μg dry matter/ml. The ICR$_{50}$ of positive control (rosmarinic acid)=2.65 μg/ml. Cosmetic Botanical Ingredient 201 is a biodegradable product.

Example 5

Preparation of Cosmetic Botanical Ingredient 301 Derived from Lavender (*Lavandula angustifolia*) Cell Serum Fractions The process for preparing Cosmetic Botanical Ingredient 301 was identical to the process described in Example 1 with regard to Cosmetic Botanical Ingredient 101, with the variations noted below. Fresh stem and leaf tissue of lavender (*Lavandula angustifolia*) was used as the plant biomass starting material. The level of dry matter in the fresh lavender plant biomass was calculated to be 13.24 percent, requiring harvesting of approximately 755 kg of fresh lavender plant biomass to yield 100 kg of dry matter. Also, the preservative and antioxidant mixture contained the following: 0.1% potassium sorbate, 0.1% sodium benzoate, 0.1% sodium methyl paraben, 0.1% citric acid, and 0.2% sodium metabisulfite. The preparation resulted in the production of 18.5 kg of Dry Matter yield (or approximately 444 liters) of Cosmetic Botanical Ingredient 301.

Example 6

Product Specifications of Cosmetic Botanical Ingredient 301 Derived from Lavender (*Lavandula angustifolia*) Cell Serum Fractions Cosmetic Botanical Ingredient 301 was prepared according to the process described above in Example 5. Analyses of Cosmetic Botanical Ingredient 301 were conducted to determine its various physico-chemical, microbial, cytotoxicity, and bioactivity characteristics, as described below. Cosmetic Botanical Ingredient 301 is a clear liquid, which has a brown-yellow color and a characteristic odor. No solvent (i.e., glycol, oil, or water) was added to the carrier medium.

Table 6 summarizes the Physical and Chemical data of Cosmetic Botanical Ingredient 301.

TABLE 6

Physical and Chemical Data

| Parameter | Method | Results |
|---|---|---|
| Solid Content, % | See Example 25, "Method 1" | 4.2 |
| Specific Gravity, g/cm$^3$ | USP <841> | 1.020 |
| Color | Gardner Scale | 11-12 |
| Refractive Index | USP <831> | 1.341 |
| pH | USP <791> | 3.9 |
| Red-Ox Potential, mV | See reference [1] | 170 |
| Conductivity, S/m | See reference [2] | 0.79 |

References:
[1] Handbook of Chemistry and Physics, 80$^{th}$ Edition, CRC Press, 1999-2000, 5-90;
[2] Handbook of Chemistry and Physics, 80$^{th}$ Edition, CRC Press, 1999-2000, 8-21, which are hereby incorporated by reference in their entirety.

Table 7 describes the UV-Spectra data regarding Cosmetic Botanical Ingredient 301.

TABLE 7

UV Spectra

| Peak | Parameter | Method | Results |
|---|---|---|---|
| #1 | Start, nm | USP <197> | 400.0 |
|  | Apex, nm | " | 260.5 |
|  | End, nm | " | 236.5 |
|  | Height, Abs | " | 2.409 |
|  | Area, Abs × nm | " | 135.505 |

Microbial analyses demonstrated that Cosmetic Botanical Ingredient 301 satisfies the cosmetic industry requirements for cosmetic ingredients with regard to CFUs and absence of pathogens (see Table 3, above, for methods).

Cosmetic Botanical Ingredient 301 was determined to be stable (i.e., maintaining physical and chemical integrity) for at least 12-18 months while stored at a temperature of between 15 and 25° C. in a closed container protected from light. No toxic effect was detected. In a controlled clinical evaluation, Cosmetic Botanical Ingredient 301 did not demonstrate 50% inhibition of neutral red uptake ($NRU_{50}$) by 3T3 fibroblasts in the concentration range 0-400 μg dry matter/ml. The $NRU_{50}$ of positive control (epidermal growth factor)>2,500 μg/ml. Cosmetic Botanical Ingredient 301 demonstrated elastase inhibitory activity, gelatinase B inhibitory activity, and superoxide scavenging ability.

Table 8, below, describes the bioactivity results regarding Cosmetic Botanical Ingredient 301.

TABLE 8

Bioactivity Results of Cosmetic Botanical Ingredient 301

| Activity | Method | $IC_{50}$ (μg/ml) | $K_i$ (μg/ml) |
|---|---|---|---|
| Elastase Inhibitory | See Example 25, "Method 5" | 36.0 | 25.4 |
| Gelantinase B inhibitory | See Example 25, "Method 6" | >100 | No data |

In a controlled clinical evaluation, Cosmetic Botanical Ingredient 301 demonstrated a 50% inhibition of cytochrome c reduction ($ICR_{50}$) at a concentration 158 μg dry matter/ml. The $ICR_{50}$ of positive control (rosmarinic acid)=26.5 μg/ml. Cosmetic Botanical Ingredient 301 is a biodegradable product.

Example 7

Preparation of Cosmetic Botanical Ingredient 401 Derived from Marigold Flower (*Calendula officinalis*) Cell Serum Fractions The process for preparing Cosmetic Botanical Ingredient 401 was identical to the process described in Example 1 with regard to Cosmetic Botanical Ingredient 101, with the variations noted below. Fresh flower tissue of marigold (*Calendula officinalis*) was used as the plant biomass starting material. The level of dry matter in the fresh marigold flower plant biomass was calculated to be 7.80 percent, requiring harvesting of approximately 1,282 kg of fresh marigold flower plant biomass to yield 100 kg of dry matter. The flowers were separated from the whole plants after cutting the plant and prior to washing. The processing of the flowers (i.e., beginning with the washing step and prior to grinding) started not more than 3 to 4 hours after cutting of the plant. Also, prior to microwave treatment of the cell serum fraction, the pH of the cell serum was first adjusted to a pH of 3.0, using a titration method utilizing 0.5 N hydrochloric acid (HCl). The preparation resulted in the production of 27.1 kg of Dry Matter yield (or approximately 704 liters) of Cosmetic Botanical Ingredient 401.

Example 8

Product Specifications of Cosmetic Botanical Ingredient 401 Derived from Marigold Flower (*Calendula officinalis*) Cell Serum Fractions Cosmetic Botanical Ingredient 401 was prepared according to the process described above in Example 7. Analyses of Cosmetic Botanical Ingredient 401 were conducted to determine its various physico-chemical, microbial cytotoxicity, and bioactivity characteristics, as described below. Cosmetic Botanical Ingredient 401 is a clear liquid, which has a light-yellow color and a light-characteristic color. No solvent (i.e., glycol, oil, or water) has been added to the carrier medium.

Table 9 describes the Physical and Chemical data of Cosmetic Botanical Ingredient 401.

TABLE 9

Physical and Chemical Data

| Parameter | Method | Results |
|---|---|---|
| Solid Content, % | See Example 25, "Method 1" | 3.9 |
| Specific Gravity, g/cm³ | USP <841> | 1.019 |
| Color | Gardner Scale | 4-5 |
| Refractive Index | USP <831> | 1.340 |
| pH | USP <791> | 3.4 |
| Red-Ox Potential, mV | See reference [1] | 160 |
| Conductivity, S/m | See reference [2] | 0.40 |

References:
[1] Handbook of Chemistry and Physics, 80$^{th}$ Edition, CRC Press, 1999-2000, 5-90;
[2] Handbook of Chemistry and Physics, 80$^{th}$ Edition, CRC Press, 1999-2000, 8-21, which are hereby incorporated by reference in their entirety.

Table 10 summarizes the UV-Spectra data for Cosmetic Botanical Ingredient 401.

TABLE 10

UV-Spectra

| Peak | Parameter | Method | Results |
|---|---|---|---|
| #1 | Start, nm | USP <197> | 400.0 |
| | Apex, nm | " | 260.0 |
| | End, nm | " | 232.5 |
| | Height, Abs | " | 1.171 |
| | Area, Abs × nm | " | 55.719 |

Microbial analyses demonstrated that Cosmetic Botanical Ingredient 401 satisfies the cosmetic industry requirements for cosmetic ingredients with regard to CFUs and absence of pathogens (see Table 3, above, for methods).

Cosmetic Botanical Ingredient 401 was determined to be stable (i.e., maintaining physical and chemical integrity) for at least 12-18 months while stored at a temperature of between 15 and 25° C. in a closed container protected from light. No toxic effect was detected. In a controlled clinical evaluation, Cosmetic Botanical Ingredient 401 did not demonstrate 50% inhibition of neutral red uptake ($NRU_{50}$) by 3T3 fibroblasts in the concentration range 0-2,500 μg dry matter/ml. The $NRU_{50}$ of positive control (epidermal growth factor) >2,500 μg/ml. Cosmetic Botanical Ingredient 401 demonstrated stimulation effect on cell proliferation and superoxide scavenging ability. In a controlled clinical evaluation, Cosmetic Botanical Ingredient 401 stimulated 3T3 fibroblasts proliferation. This 10-15% stimulation was observed over a range from 5 to 100 μg dry matter/ml. The stimulation by positive control (epidermal growth factor)=20-30%. In a controlled clinical evaluation, Cosmetic Botanical Ingredient 401 demonstrated superoxide scavenging activity resulting in 50% inhibition of cytochrome c reduction ($ICR_{50}$) at a concentration 153 μg dry matter/ml. The $ICR_{50}$ of positive control (rosmarinic acid)=26.5 μg/ml. Cosmetic Botanical Ingredient 401 is a biodegradable product.

Example 9

Preparation of Cosmetic Botanical Ingredient 501 Derived from Sage (*Salvia officinalis*) Cell Serum Fractions The process for preparing Cosmetic Botanical Ingredient 501 was identical to the process described in Example 1 with regard to Cosmetic Botanical Ingredient 101, with the variations noted below. Fresh stem and leaf tissue of sage (*Salvia officinalis*) was used as the plant biomass starting material. The level of dry matter in the fresh sage plant biomass was calculated to be 10.64 percent, requiring harvesting of approximately 940 kg of fresh sage plant biomass to yield 100 kg of dry matter. Prior to microwave treatment of the cell serum fraction, the pH of the cell serum was first adjusted to a pH of 3.0, using a titration method with 0.5 N hydrochloric acid (HCl). Also, the preservative and antioxidant mixture contained the following: 0.1% potassium sorbate, 0.1% sodium benzoate, 0.1% sodium methyl paraben, 0.1% citric acid, and 0.2% sodium metabisulfite. The preparation resulted in the production of 14.9 kg of Dry Matter yield (or approximately 370 liters) of Cosmetic Botanical Ingredient 501.

Example 10

Product Specifications of Cosmetic Botanical Ingredient 501 Derived from Sage (*Salvia officinalis*) Cell Serum Fractions Cosmetic Botanical Ingredient 501 was prepared according to the process described above in Example 9. Analyses of Cosmetic Botanical Ingredient 501 were conducted to determine its various physico-chemical, microbial, cytotoxicity, and bioactivity characteristics, as described below. Cosmetic Botanical Ingredient 501 is a clear liquid, which has a brown-yellow color and a characteristic odor. No solvent (i.e., glycol, oil, or water) was added to the carrier medium.

Table 11 describes the Physical and Chemical data of Cosmetic Botanical Ingredient 501.

TABLE 11

Physical and Chemical Data

| Parameter | Method | Results |
|---|---|---|
| Solid Content, % | See Example 25, "Method 1" | 4.0 |
| Specific Gravity, g/cm$^3$ | USP <841> | 1.021 |
| Color | Gardner Scale | 8-9 |
| Refractive Index | USP <831> | 1.340 |
| pH | USP <791> | 3.2 |
| Red-Ox Potential, mV | See reference [1] | 190 |
| Conductivity, S/m | See reference [2] | 0.99 |

References:
[1] Handbook of Chemistry and Physics, 80$^{th}$ Edition, CRC Press, 1999-2000, 5-90;
[2] Handbook of Chemistry and Physics, 80$^{th}$ Edition, CRC Press, 1999-2000, 8-21, which are hereby incorporated by reference in their entirety.

Table 12 summarizes the UV-Spectra data for Cosmetic Botanical Ingredient 501.

TABLE 12

UV-Spectra

| Peak | Parameter | Method | Results |
|---|---|---|---|
| #1 | Start, nm | USP <197> | 400.0 |
|  | Apex, nm | " | 330.0 |
|  | End, nm | " | 306.5 |
|  | Height, Abs | " | 0.260 |
|  | Area, Abs × nm | " | 14.952 |
| #2 | Start, nm | USP <197> | 306.5 |
|  | Apex, nm | " | 259.0 |
|  | End, nm | " | 235.0 |
|  | Height, Abs | " | 1.248 |
|  | Area, Abs × nm | " | 57.844 |

Microbial analyses demonstrated that Cosmetic Botanical Ingredient 501 satisfies the cosmetic industry requirements for cosmetic ingredients with regard to CFUs and absence of pathogens (see Table 3, above, for methods).

Cosmetic Botanical Ingredient 501 was determined to be stable (i.e., maintaining physical and chemical integrity) for at least 12-18 months while stored at a temperature of between 15 and 25° C. in a closed container protected from light. No toxic effect was detected. In a controlled clinical evaluation, Cosmetic Botanical Ingredient 501 did not demonstrate 50% of neutral red uptake (NRU$_{50}$) by 3T3 fibroblasts in the concentration range 0-2,430 µg dry matter/ml. The NUR$_{50}$ of positive control (epidermal growth factor)>2,500 µg/ml. Cosmetic Botanical Ingredient 501 demonstrated elastase inhibitory activity, gelatinase B inhibitory activity, and superoxide scavenging ability. (See Table 13, below.)

TABLE 13

Bioactivity Results of Cosmetic Botanical Ingredient 501

| Activity | Method | IC$_{50}$ (µg/ml) | K$_{ii}$ (µg/ml) |
|---|---|---|---|
| Elastase Inhibitory | See Example 25, "Method 5" | 115.0 | 70.3 |
| Gelatinase B Inhibitory | See Example 25, "Method 6" | >100 | No data |

In a controlled clinical evaluation, Cosmetic Botanical Ingredient 501 demonstrated superoxide scavenging activity, resulting in 50% inhibition of cytochrome c reduction (ICR$_{50}$) at a concentration >160 µg dry matter/ml. The ICR$_{50}$ of positive control (rosmarinic acid)=26.5 µg/ml. Cosmetic Botanical Ingredient 501 is a biodegradable product.

Example 11

Preparation of Cosmetic Botanical Ingredient 402 Derived from Marigold Flower (*Calendula officinalis*) Membrane Fractions The process for preparing Cosmetic Botanical Ingredient 402 was identical to the process described in Example 7 with regard to Cosmetic Botanical Ingredient 401, with the variations noted below. Once the membrane fraction (precipitate) was separated from the filtered cell juice, the process described in Example 7 was no longer followed. Instead, the membrane fraction was treated to yield Cosmetic Botanical Ingredient 402, as described below.

Treatment of Membrane Fraction to Produce Cosmetic Botanical Ingredient 402. The membrane fraction was stabilized and incorporated into a polymer matrix. This was performed immediately after separation of the membrane fraction from cell juice. To prepare approximately 100 grams of Cosmetic Botanical Ingredient 402, the cell membrane fraction was stabilized by mixing it with non-ionic emulsifier Polysorbate 80 (Tween 80) and antioxidants (Tenox 4). Specifically, 20 grams of fresh membrane fraction was mixed vigorously with 3.5 grams of Tween 80 and 0.1 gram of Tenox 4 (solution of Butylated Hydroxyanisole and Butylated Hydroxytoluene in oil) until homogeneous, while avoiding aeration during mixing.

Once stabilized, the membrane fraction was incorporated into a polymer matrix (i.e., a dispersion of polymeric emulsifier, acrylates/C10-C30 acrylate crosspolymer). The polymer matrix was prepared by dispersing 0.9 grams of Pemulen TR-2 in 69.2 grams of warm deionized water and mixing until uniform using moderate agitation, while avoiding aeration. In parallel, 5 grams of Glycerin and 1.0 gram of Phenonip (mixture of Phenoxyethanol (and) Methylparaben (and) Butylparaben (and) Ethylparaben (and) Propylparaben) were combined in a separate vessel and mixed until uniform. With moderate agitation, the phases containing Pemulen and Glycerin with Phenonip were combined and mixed until uniform. To incorporate the membrane fraction into the polymer matrix, the phase containing the membrane fraction, Tween 80, and Tenox 4 was added to the phase containing the Pemulen, Glycerin, and Phenonip, and then mixed with vigorous agitation while avoiding aeration. Stabilization of the membrane fraction mixture was achieved by neutralizing it with 18% aqueous solution of sodium hydroxide (NaOH) and mixed vigorously to produce a uniform system having a pH of 5.0±0.4. This preparation, which started from 100 kg of fresh marigold flower plant biomass (approximately 1,282 kg of fresh marigold flower biomass having 7.80 percent dry matter), resulted in the production of 9.5 kg of Dry Matter yield (or approximately 205 liters) of Cosmetic Botanical Ingredient 402, which was used for characterization of its physicochemical and bioactive qualities. The recommended storage conditions for Cosmetic Botanical Ingredient 402 include storage in a closed container protected from light at a temperature between 2 and 8° C.

Example 12

Product Specifications of Cosmetic Botanical Ingredient 402 Derived from Marigold Flower (*Calendula officinalis*) Membrane Fractions Cosmetic Botanical Ingredient 402 was prepared according to the process described above in Example 11. Analyses of Cosmetic Botanical Ingredient 402 were conducted to determine its various physico-chemical, microbial, cytotoxicity, and bioactivity characteristics, as described below. Cosmetic Botanical Ingredient 402 is an opaque gel, which has an orange color and light-characteristic odor. Cosmetic Botanical Ingredient 402 was formulated utilizing the natural cell juice constituents gelled with a polymer to assure the highest level of purity uniformity, compatibility, stability, safety and efficacy.

Table 14 describes the Physical and Chemical data of Cosmetic Botanical Ingredient 402.

TABLE 14

Physical and Chemical Data

| Parameter | Method | Results |
| --- | --- | --- |
| Non-Volatile Residue (NVR), % | See Example 25, "Method 2" | 7.1 |
| Specific Gravity, g/cm$^3$ | USP <841> | 1.054 |
| Viscosity, cps | USP <911> | 15,800 |
| pH | USP <791> | 4.6 |
| Total Carotenoids, % NVR | See Example 25, "Method 4" | 0.86 |
| Lutein, % NVR | See Example 25, "Method 4" | 0.83 |

Table 15 summarizes the L*a*b* values data regarding Cosmetic Botanical Ingredient 402.

TABLE 15

L*a*b* Values

| Parameter | Method | Results |
| --- | --- | --- |
| L* | See Example 25, "Method 3" | 33.27 |
| a* | See Example 25, "Method 3" | 20.36 |
| b* | See Example 25, "Method 3" | 49.56 |

Microbial analyses demonstrated that Cosmetic Botanical Ingredient 402 satisfies the cosmetic industry requirements for cosmetic ingredients with regard to CFUs and absence of pathogens (see Table 3, above, for methods).

Cosmetic Botanical Ingredient 402 was determined to be stable (i.e., maintaining physical and chemical integrity) for at least 12-18 months while stored at a temperature of between 2 and 8° C. in a closed container protected from light. Cosmetic Botanical Ingredient 402 is a biodegradable product. No toxic effect was detected. In a controlled clinical evaluation, Cosmetic Botanical Ingredient 402 did not demonstrate 50% inhibition of neutral red uptake ($NRU_{50}$) by 3T3 fibroblasts in the concentration range 0-354 µg dry matter/ml. The $NRU_{50}$ of positive control (epidermal growth factor)>2,500 µg/ml. Cosmetic Botanical Ingredient 402 demonstrates elastase inhibitory activity and trypsin inhibitory activity. Table 16 summarizes certain bioactivity results for Cosmetic Botanical Ingredient 402.

TABLE 16

Bioactivity Results of Cosmetic Botanical Ingredient 402

| Activity | Method | $IC_{50}$ (µg/ml) | $K_i$ (µg/ml) |
| --- | --- | --- | --- |
| Elastase Inhibitory | See Example 25, "Method 5" | 21.0 | 0.68 |
| Trypsin Inhibitory | See reference [1] | 5.6 | No data |

Reference: [1] Cannel R. J. P., Kellam S. J., Owsianka A. M., Walker J. M. Planta Medica, 1988, v. 54, pp. 10-14, which is hereby incorporated by reference in its entirety.

Example 13

Preparation of Cosmetic Botanical Ingredient 502 Derived from Sage (*Salvia officinalis*) Membrane Fractions The process for preparing Cosmetic Botanical Ingredient 502 was identical to the process described in Example 11 with regard to Cosmetic Botanical Ingredient 402, with the variations noted below. Fresh stem and leaf tissue of sage (*Salvia officinalis*) was used as the plant biomass starting material. The level of dry matter in the fresh sage plant biomass was calculated to be 10.64 percent, requiring harvesting of approximately 940 kg of fresh sage plant biomass to yield 100 kg of dry matter. This preparation resulted in the production of 6.7 kg of Dry Matter yield (or approximately 124 liters) of Cosmetic Botanical Ingredient 502.

Example 14

Product Specifications of Cosmetic Botanical Ingredient 502 Derived from Sage (*Salvia officinalis*) Membrane Fractions Cosmetic Botanical Ingredient 502 was prepared according to the process described above in Example 13. Analyses of Cosmetic Botanical Ingredient 502 were conducted to determine its various physico-chemical, microbial, cytotoxicity, and bioactivity characteristics, as described below Cosmetic Botanical Ingredient 502 is an opaque gel, which has a green color and characteristic odor. Cosmetic Botanical Ingredient 502 has been formulated utilizing the natural cell juice constituents gelled with a polymer to assure the highest level of purity uniformity, compatibility, stability, safety and efficacy.

Table 17 describes the Physical and Chemical data of Cosmetic Botanical Ingredient 502.

TABLE 17

Physical and Chemical Data

| Parameter | Method | Results |
|---|---|---|
| Non-Volatile Residue, % | See Example 25, "Method 2" | 8.3 |
| Specific Gravity, g/cm$^3$ | USP <841> | 1.047 |
| Viscosity, cps | USP <911> | 5.200 |
| pH | USP <791> | 4.6 |

Table 18 describes the L*a*b* values for Cosmetic Botanical Ingredient 502.

TABLE 18

L*a*b* Values

| Parameter | Method | Results |
|---|---|---|
| L* | See Example 25, "Method 3" | 27.35 |
| a* | See Example 25, "Method 3" | −1.4 |
| b* | See Example 25, "Method 3" | 16.97 |

Microbial analyses demonstrated that Cosmetic Botanical Ingredient 502 satisfies the cosmetic industry requirements for cosmetic ingredients with regard to CFUs and absence of pathogens (see Table 3, above, for methods).

Cosmetic Botanical Ingredient 502 was determined to be stable (i.e., maintaining physical and chemical integrity) for at least 12-18 months while stored at a temperature of between 2 and 8° C. in a closed container protected from light. Cosmetic Botanical Ingredient 502 is a biodegradable product. No toxic effect was detected. Cosmetic Botanical Ingredient 502 demonstrates elastase inhibitory activity and gelatinase B inhibitory activity. (See Table 19, below.)

TABLE 19

Bioactivity Results for Cosmetic Botanical Ingredient 502

| Activity | Method | IC$_{50}$ (µg/ml) | K$_i$ (µg/ml) |
|---|---|---|---|
| Elastase Inhibitory | See Example 25, "Method 5" | 30.0 | 12.0 |
| Gelatinase B Inhibitory | See Example 25, "Method 6" | <25.0 | No data |

Example 15

Distribution of Dry Matter Regarding Preparation of Cosmetic Botanical Ingredients From Alfalfa, Barley, Lavender, Marigold Flowers, and Sage Various fractions collected during the production of Cosmetic Botanical Ingredients 101, 201, 301, 401, 402, 501, and 502 were analyzed and compared for dry matter distribution.

Table 20 shows the distribution of 100 kg dry mater between the cell juices and press-cakes of the various processes. It was determined that the process of the present invention permits extracted yield conversion into plant cell juices in the range of from about 20 to 40 percent of initial biomass dry matter.

TABLE 20

Distribution of 100 kg Dry Matter Between Cell Juices and Press-Cakes

| | Plant Source | | | | |
|---|---|---|---|---|---|
| Product | Alfalfa | Barley | Lavender | Marigold Flowers | Sage |
| Fresh Biomass | 100.0 | 100.0 | 100.0 | 100.0 | 100.0 |
| Cell Juice | 32.7 | 28.5 | 28.1 | 37.6 | 21.9 |
| Press-Cake | 67.3 | 71.5 | 71.9 | 62.4 | 78.1 |

Table 21 shows that the yield of membrane fractions' dry matter was in the range from 6% to 13% of initial biomass dry matter and from 25% to 45% of cell juice dry matter. Based on high dry matter yield, membrane fractions were selected as a prospective source for preparation of multiphase cosmetic ingredients.

TABLE 21

Distribution of Dry Matter between Membrane Fractions and Cell Juice Supernatants

| | Plant Source | | | | |
|---|---|---|---|---|---|
| Product | Alfalfa | Barley | Lavender | Marigold Flowers | Sage |
| Fresh Biomass | 100.0 | 100.0 | 100.0 | 100.0 | 100.0 |
| Cell Juice | 32.7 | 28.5 | 28.1 | 37.6 | 21.9 |
| Membrane Fraction | 12.2 | 12.9 | 8.7 | 9.5 | 6.7 |
| Cell Juice Supernatant | 20.5 | 15.6 | 19.4 | 28.1 | 15.2 |

The process of the present invention permitted the following distribution of dry matter between cytoplasm fractions and cell serum (see Table 22).

TABLE 22

Distribution of Dry Matter between Cytoplasm Fractions and Cell Serum

| | Plant Source | | | | |
|---|---|---|---|---|---|
| Product | Alfalfa | Barley | Lavender | Marigold Flowers | Sage |
| Fresh Biomass | 100.0 | 100.0 | 100.0 | 100.0 | 100.0 |
| Cell Juice | 32.7 | 28.5 | 28.1 | 37.6 | 21.9 |
| Cell Juice Supernatant | 20.5 | 15.6 | 19.4 | 28.1 | 15.2 |
| Cytoplasm Fraction | 2.3 | 0.4 | 0.8 | 0.9 | 0.2 |
| Cell Serum | 18.2 | 15.2 | 18.6 | 27.2 | 15.0 |

Table 22 shows that the yield of cytoplasm fractions dry matter did not exceed 2.5% of initial biomasses dry matter and subsequently 11% of cell juice supernatant dry matter. Most of cell juice supernatant dry matter was concentrated in cell sera: 88.8% (alfalfa), 97.4% (barley), 95.9% (lavender), 96.8% (marigold flowers), and 98.7% (sage). Based on high dry matter yield, cell sera were selected as a prospective source for preparation of soluble cosmetic ingredients.

Example 16

Optimum Composition of Preservatives and Antioxidants for Cosmetic Botanical Ingredients From Alfalfa, Barley, Lavender, Marigold Flowers, and Sage The optimum composition of preservatives and antioxidant was determined to be very similar for all plant sources (i.e., from alfalfa, barley, lavender, marigold flowers, and sage (see Table 23).

TABLE 23

Optimum Composition of Preservatives and Antioxidant (%) Required for Stabilization of Cell Serum Filtrates

| | Plant Source | | | | |
|---|---|---|---|---|---|
| Component | Alfalfa | Barley | Lavender | Marigold Flowers | Sage |
| Preservatives | | | | | |
| Potassium Sorbate | 0.1 | 0.1 | 0.1 | 0.1 | 0.1 |
| Sodium Benzoate | 0.1 | 0.1 | 0.1 | 0.1 | 0.1 |
| Sodium Methyl Paraben | 0.1 | 0.1 | 0.1 | 0.1 | 0.1 |
| Citric Acid | — | — | 0.1 | — | 0.1 |
| Anti-oxidant | | | | | |
| Sodium Metabisulfite | 0.2 | 0.2 | 0.2 | 0.1 | 0.2 |

Example 17

Comparison of Various Characteristics of Cosmetic Botanical Ingredients From Alfalfa, Barley, Lavender, Marigold Flowers, and Sage The physico-chemical, spectral, microbial, toxicological, performance and efficacy data related to cosmetic botanical ingredients are presented in Tables 24 and 25.

TABLE 24

Physical and Chemical Properties of Cosmetic Ingredients Produced from Cell Serums

| | Cosmetic Botanical Ingredient and Plant Source | | | | |
|---|---|---|---|---|---|
| Parameter | 101 Alfalfa | 201 Barley | 301 Lavender | 401 Marigold Flowers | 501 Sage |
| Solid Content, % | 5.3 | 3.5 | 4.2 | 3.9 | 4.0 |
| Specific Gravity, g/cm³ | 1.025 | 1.019 | 1.020 | 1.019 | 1.021 |
| Color | 6-7 | 5-6 | 11-12 | 4-5 | 8-9 |
| Refractive Index | 1.342 | 1.338 | 1.341 | 1.340 | 1.340 |
| pH | 4.1 | 4.1 | 3.9 | 3.4 | 3.2 |
| Red-Ox Potential, mV | 70 | 95 | 170 | 160 | 190 |
| Conductivity, S/m | 0.96 | 1.09 | 0.79 | 0.40 | 0.99 |

TABLE 25

UV-Spectral Properties of Cosmetic Ingredients Produced from Cell Serums

| | | Cosmetic Botanical Ingredient and Plant Source | | | | |
|---|---|---|---|---|---|---|
| Peak | Parameter | 101 Alfalfa | 201 Barley | 301 Lavender | 401 Marigold Flowers | 501 Sage |
| 1 | Start, nm | 400.0 | 400.0 | 400.0 | 400.0 | 400.0 |
| | Apex, nm | 324.5 | 335.5 | 260.5 | 260.0 | 330.0 |
| | End, nm | 303.0 | 305.0 | 236.5 | 232.5 | 306.5 |
| | Height, Abs | 0.347 | 0.232 | 2.409 | 1.171 | 0.260 |
| | Area, Abs × nm | 21.197 | 14.254 | 135.505 | 55.719 | 14.952 |
| 2 | Start, nm | 303.0 | 305.0 | — | — | 306.5 |
| | Apex, nm | 258.0 | 258.0 | — | — | 259.0 |
| | End, nm | 233.0 | 233.0 | — | — | 235.0 |
| | Height, Abs | 1.471 | 1.268 | — | — | 1.248 |
| | Area, Abs × nm | 65.103 | 55.631 | — | — | 57.844 |

The data presented in Table 24 and Table 25 demonstrates that although five plant source raw materials were used (even belonging to different plant families), the properties of the cosmetic botanical ingredients produced from a variety of cell sera are very similar. This similarity can be very valuable for manufacturing of highly standardized natural products based on the cosmetic botanical ingredients described above.

The data presented in Table 26 demonstrate that all tested cosmetic botanical ingredients satisfy the cosmetic industry requirement to the CFU level (colony forming units). The absence of pathogens also satisfied the industry requirements to the safety of cosmetic ingredients.

TABLE 26

Microbial Data of Cosmetic Ingredients Produced from Cell Serums

| | Cosmetic Botanical Ingredient and Plant Source | | | | |
|---|---|---|---|---|---|
| Parameter | 101 Alfalfa | 201 Barley | 301 Lavender | 401 Marigold Flowers | 501 Sage |
| Colony Forming Units (CFU) per gram of sample | <100 | <100 | <100 | <100 | <100 |
| E. coli | Negative | Negative | Negative | Negative | Negative |
| Candida albicans | Negative | Negative | Negative | Negative | Negative |
| Pseudomonas sp. | Negative | Negative | Negative | Negative | Negative |
| Staphylococcus aureus | Negative | Negative | Negative | Negative | Negative |

In addition, the cosmetic botanical ingredients demonstrated absence of cytotoxicity in the wide concentration ranges. As an example, a test involving neutral red uptake (NRU) by 3T3 fibroblasts, which is commonly used for determination of cytotoxicity, was utilized to assess cytotoxicity of cosmetic botanical ingredients. The NRU value is proportional to the number of viable cells in this in vitro test population. It was found that 50% inhibition of neutral red uptake ($NRU_{50}$) by 3T3 fibroblasts was not reached even at very high concentrations of tested cosmetic ingredients. As a comparison with respect to the safety profile, most of the cosmetic botanical ingredients produced by the described methods were close to Epidermal Growth Factor (EGF) as used as a positive control (see Table 27).

TABLE 27

Cytotoxicity Data of Cosmetic Ingredients Produced from Cell Serums and Epidermal Growth Factor (EGF)

| | Cosmetic Botanical Ingredient and Plant Source | | | | | |
|---|---|---|---|---|---|---|
| Parameter | 101 Alfalfa | 201 Barley | 301 Lavender | 401 Marigold Flowers | 501 Sage | Positive Control EGF |
| $NRU_{50}$, µg Dry Matter/mL | >2,500 | >2,500 | >400 | >2,500 | 2,430 | >2,500 |
| Cell Morphology* | NCM | NCM | MLT | NCM | NCM | NCM |

*NCM: Normal Cell Morphology; MLT: Moderate Level of Toxicity.

The cosmetic botanical ingredients produced from cell sera have significantly higher safety profile when compared with water extract isolated by conventional method from the same batch of dried raw material or commercial extract obtained from the same plant source. As an example, the data related to marigold flowers presented in the table below (see Table 28).

TABLE 28

Cytotoxicity Data of Cosmetic Botanical Ingredient 402, Water Extract and Commercial Extract Isolated from Marigold Flowers

| | Tested Product | | | |
|---|---|---|---|---|
| Parameter | Cosmetic Botanical Ingredient 402 | Water Extract | Commercial Extract | EGF |
| $NRU_{50}$, µg Dry Matter/mL | >2,500 | 41 | 2 | >2,500 |
| Cell Morphology* | NCM | HLT | HLT | NCM |

*NCM: Normal Cell Morphology; HLT: High Level of Toxicity.

All cosmetic botanical ingredients produced from cell sera demonstrated anti-oxidant properties or more specifically superoxide scavenging ability. As an example, the concentrations required to inhibit 50% of cytochrome c reduction ($ICR_{50}$) were determined and rosmarinic acid (RA) was used as a positive control (see Table 29).

TABLE 29

Superoxide Scavenging Ability of Cosmetic Ingredients Produced from Cell Serums and Rosmarinic Acid

| | Cosmetic Botanical Ingredient and Plant Source | | | | | Positive Control Rosmarinic Acid |
|---|---|---|---|---|---|---|
| | 101 Alfalfa | 201 Barley | 301 Lavender | 401 Marigold Flowers | 501 Sage | |
| $ICR_{50}$, µg Dry Matter/mL | 149 | 160 | 158 | 153 | 160 | 26.5 |

Example 18

Characterization of Cosmetic Ingredients Produced from Membrane Fraction

The physico-chemical, optical, microbial, toxicological, performance and efficacy data related to selected cosmetic ingredients produced from membrane fractions are presented in Tables 30 and 31.

TABLE 30

Physico-Chemical Properties of Cosmetic Ingredients Produced from Membrane Fractions

| | Cosmetic Botanical Ingredient and Plant Source | |
|---|---|---|
| Parameter | 402 Marigold Flowers | 502 Sage |
| Non-Volatile Residue, % | 7.1 | 8.3 |
| Specific Gravity, g/cm³ | 1.054 | 1.047 |
| Viscosity, cps | 15,800 | 5,200 |
| pH | 4.6 | 4.6 |

TABLE 31

L*a*b* Values of Cosmetic Ingredients Produced from Membrane Fractions

| | Cosmetic Botanical Ingredient and Plant Source | |
|---|---|---|
| | 402 Marigold Flowers | 502 Sage |
| L* | 33.27 | 27.35 |
| a* | 20.36 | −1.4 |
| b* | 49.56 | 16.97 |

The data presented in Table 30 and Table 31 demonstrate significant differences between properties of cosmetic ingredients produced from membrane fractions obtained from leaf-and-stalk biomass (sage) and from flowers (marigold). Generally, the above reflects the difference between chloroplasts, which are predominantly concentrated in sage membrane fraction, and chromoplasts, which are predominantly concentrated in marigold flowers.

Microbial analyses demonstrated that Cosmetic Botanical Ingredients 402 and 502 satisfy the cosmetic industry requirements for cosmetic ingredients with regard to CFUs and absence of pathogens (see Table 3, above, for methods).

Example 19

Anti-Inflammatory and Antioxidant Analysis of Cosmetic Botanical Ingredients Objectives and Rationale for Selected Experimental Models Cosmetic Botanical Ingredients 101, 102, 201, 202, 301, 302, 401, 402, 501, and 502, as well as others, were analyzed for their anti-inflammatory and antioxidant qualities. The results of these analyses are summarized in this Example 19, below. The procedures and results are explained in Examples 20-24, below.

The described procedure pertains to the distribution of concentrated serum-derived and membrane-derived cosmetic botanical ingredients. These ingredients demonstrated two important activities (antiproteolytic activity and antioxidant activity) towards reducing connective tissue damage associated with inflammation. The pattern of distribution for antiproteolytic activity is selectively in the membrane fractions and subsequently in multiphase botanical cosmetic ingredients, where as the distribution pattern for antioxidant activity is selectively in the serum fraction and subsequently soluble in cosmetic ingredients. Membrane-derived cosmetic ingredients contain components which inhibit both of the two major classes of destructive proteinases, i.e., serine proteinases exemplified by neutrophil elastase and matrix metalloproteinases exemplified by gelatinase B. The potential of the membrane-derived cosmetic ingredients to achieve inhibition of the synergistic proteolytic activities of inflammatory cells merits consideration of their use in topical applications for anti-inflammatory formulations. The mode of inhibition of these cosmetic ingredients suggests that their effects are reversible, and, they would not cause undesirable long term modifications to defense or repair mechanisms.

The selective distribution of antioxidant activities into the serum-derived cosmetic ingredients presents an additional direction to incorporate an important biological activity which reduces damage caused by the reactive oxygen species generated by inflammatory cells. The serum-derived cosmetic ingredients obtained from multiple botanical sources possess potent modulatory activities which diminish the capacity of the inflammatory cells to generate reactive oxygen species rather than simply neutralizing the oxidants. The described method employed in generation of the serum-derived cosmetic ingredients result in the preservation of this modulatory activity along with scavenging activity. The conventional procedures for obtaining aqueous extracts simply achieve only some distribution of scavenging activity alone.

The selective distribution of one type of biological activity into the membrane-derived cosmetic ingredient and another activity into the serum-derived cosmetic ingredient obtained from the same botanical sources represents an opportunity to employ novel topical formulations in which two phases are maintained in stable composition.

Cosmetic Botanical Ingredients 101, 201, 301, 401, 402, 501, and 502 (collectively referred to herein as the "Cosmetic Botanical Ingredients") were evaluated for their anti-inflammatory and antioxidant activities. There are multiple mechanisms for injury to connective tissue that may arise as a consequence of the inflammatory process. The one final common pathway leading to inflammatory tissue injury involves destruction of the components of the stroma by white blood cell-derived proteolytic enzymes. Accordingly, assays were employed to evaluate the capacity of the different Cosmetic Botanical Ingredients to inhibit these inflammatory proteinases. In the evaluation, two proteinases were used: neutrophil elastase and neutrophil gelatinase. These two enzymes degrade the components of the extracellular matrix of human connective tissue in a synergistic manner. Moreover, neutrophil elastase can inactivate the body's own inhibitory defenses against neutrophil gelatinase while conversely, the gelatinase can inactivate the body's own antielastase defenses. Thus, cosmetic botanical ingredients which can inhibit these two enzymes provide significant protection against inflammatory injury. The assays selected permit quantitation of the inhibitory activity of these cosmetic botanical ingredients and provide information regarding some basic features of the mode of inhibition.

In addition to degradative proteinases, inflammatory processes are often associated with release of reactive oxygen species from the activated cells. These reactive species include superoxide anions, hydroxyl radicals, hydrogen peroxide, and hypochlorous acid. The biological effects of these oxidants can lead to inactivation of important endogenous antiproteolytic defenses in the human tissue. Assays were employed which measure the capacity of the cosmetic botanical ingredients to lower the levels of reactive oxygen species released by activated inflammatory cells. Additionally, assays were used to quantitate the capacity of the cosmetic botanical ingredients to neutralize reactive oxygen species of endogenous and exogenous origins.

Example 20

Evaluation of Anti-Elastase Activity

During the inflammatory process, elastase activity is directly related to the actions of multiple enzymes, but neutrophil elastase is presented at the highest concentrations and is the most active proteinase against the widest variety of connective tissue components, including elastin. In the evaluation assay, inhibition of this enzyme employed a synthetic soluble peptide substrate (Methoxysuccinyl-Ala-Ala-Pro-Val-p-Nitroanilide) that is specific for neutrophil elastase. The source of neutrophil elastase was a purified enzyme preparation derived from the airway secretions of patients with cystic fibrosis. Analysis of the concentration dependence of inhibition leads to the quantitation of potency of the inhibitory activity. This activity is expressed as that concentration of dry matter within each cosmetic botanical ingredient required to achieve 50% inhibition ($IC_{50}$). In addition, the value of the inhibition constant, $K_i$, was determined. Graphical analysis of the inhibition data also provides the information related to the mode of inhibition (reversible or irreversible). Since neutrophil elastase has positive physiological roles when present at controlled levels, indiscriminate use of irreversible inhibitors may compromise these normal functions of the enzyme.

Table 32 describes the results of the in vitro elastase inhibition studies of the serum-derived and membrane-derived cosmetic ingredients.

TABLE 32

Elastase Inhibition Evaluation of Cosmetic Botanical Ingredients

| Cosmetic Botanical Ingredient (Source) | $IC_{50}$ µg/ml | $K_i$ µg/ml |
|---|---|---|
| 101 (Alfalfa Serum Fraction) | No Inhibition | No Inhibition |
| 102 (Alfalfa Membrane Fraction) | 9.5 | 7.2 |
| 201 (Barley Serum Fraction) | No Inhibition | No Inhibition |
| 202 (Barley Membrane Fraction) | 4.6 | 3.6 |
| 301 (Lavender Serum Fraction) | 36.0 | 25.4 |

TABLE 32-continued

Elastase Inhibition Evaluation of Cosmetic Botanical Ingredients

| Cosmetic Botanical Ingredient (Source) | $IC_{50}$ µg/ml | $K_i$ µg/ml |
|---|---|---|
| 302 (Lavender Membrane Fraction) | 10.0 | 2.3 |
| 401 (Marigold Flowers Serum Fraction) | No Inhibition | No Inhibition |
| 402 (Marigold Flowers Membrane Fraction) | 21.0 | 0.68 |
| 501 (Sage Serum Fraction) | 115.0 | 70.3 |
| 502 (Sage Membrane Fraction) | 30.0 | 12.0 |
| Positive Control (Elhibin ®) | 4.0 | 3.4 |

Elastase inhibition activity has been identified predominantly in cosmetic ingredients obtained from membrane fractions. Cosmetic ingredients produced from alfalfa, barley and marigold flowers serum fractions did not display any elastase inhibition. Cosmetic ingredients obtained from lavender and sage serum fractions did show much lower inhibitory activity compared with corresponding cosmetic ingredients obtained from membrane fractions. The above pattern of distribution of elastase inhibition activity between the membrane-derived and serum-derived cosmetic botanical ingredients was found for all tested raw material sources.

Selected cosmetic ingredients obtained from membrane fractions demonstrate elastase inhibition activity which is comparable in magnitude with the activity of a specific elastase inhibitor used as a positive control.

Cosmetic ingredients obtained from membrane fractions demonstrated properties consistent with "classical" simple competitive and reversible elastase inhibitors, while the positive control has a complex inhibitory behavior (including some irreversible inhibitory activity).

The inhibitory properties of cosmetic ingredients produced from membrane fractions toward the most destructive inflammatory proteinase (neutrophil elastase) qualifies these ingredients as valuable components of topical products for use as anti-inflammatory agents.

Example 21

Elastase Inhibition Evaluation of the Marigold Products

The in vitro elastase inhibition evaluation of marigold products are described below and summarized in Table 33.

TABLE 33

Elastase Inhibition Evaluation of Marigold Products

| Cosmetic Botanical Ingredient (Source) and Extract | $IC_{50}$ µg/ml | $K_i$ µg/ml |
|---|---|---|
| 401 (Marigold Flowers Serum Fractions) | No Inhibition | No Inhibition |
| 402 (Marigold Flowers Membrane Fractions) | 21.0 | 0.68 |
| Commercial Extract (Marigold Flowers) | 120.0 | 152.0 |
| Conventional Extract (Marigold Flowers) | No Inhibition | No Inhibition |

Cosmetic ingredient 402, obtained from marigold flowers membrane fraction, demonstrated the highest elastase inhibition activity, but the cosmetic ingredient 401 obtained from serum fraction, which was derived from the same raw material and separated from membrane fraction during cell juice fractionation process, has no detectable inhibition activity.

The water extract which was produced by conventional extraction methods was obtained from the same batch of raw material and did not display elastase inhibition activity.

The commercial extract, which was derived from same raw material, displayed only minimal anti-elastase activity.

The cosmetic ingredient 402 derived from same raw material displayed anti-elastase activity by about two orders of magnitude over that of the commercial extract.

Example 22

Evaluation of Anti-Gelatinase Activity of the Cosmetic Botanical Ingredients

Neutrophils contain two major enzymes from the class of matrix metalloproteinases, which collectively are implicated in extensive connective tissue destruction: neutrophil collagenase (MMP-8) and gelatinase B (MMP-9). Because elastase has poor activity against native collagen, and neutrophil collagenase alone cannot solubilize the connective tissue protein by itself, gelatinase B is considered as a major contributor to inflammatory injury to the extracellular matrix. A specific assay for this enzyme was used to evaluate the potential of cosmetic botanical ingredients to inhibit degradation of the extracellular matrix mediated by inflammatory cell-derived matrix metalloproteinases. Gelatinase B activity was detected by hydrolysis of a low molecular weight synthetic substrate (APMA). Inhibitors of gelatinase B diminish the accelerating rate of enzyme reaction product formation in a dose-dependent fashion. Such enzyme inhibition was found when tested cosmetic ingredients were added to the reaction mixture.

The anti-gelatinase B data regarding the Cosmetic Botanical Ingredients is described below and summarized in Table 34.

TABLE 34

In Vitro Gelatinase B Inhibition Evaluation of Cosmetic Botanical Ingredients.

| Cosmetic Botanical Ingredient (Source) | % Inhibition [100 µg/ml] |
|---|---|
| 101 (Alfalfa Serum Fraction) | 20 |
| 201 (Barley Serum Fraction) | 32 |
| 301 (Lavender Serum Fraction) | 21 |
| 401 (Marigold Flowers Serum Fraction) | 42 |
| 501 (Sage Serum Fraction) | 29 |
| 502 (Sage Membrane Fraction) | 100 |
| Positive Control (Rosmarinic Acid) | 91 |

All serum-derived cosmetic botanical ingredients have demonstrated modest gelatinase B inhibition activity.

Cosmetic Botanical Ingredient 502 obtained from the sage membrane fraction demonstrated significant gelatinase B inhibition activity, which exceeded by at least three times the corresponding activity of the serum-derived cosmetic ingredient. The pattern of distribution of gelatinase B inhibitory activity between membrane-derived and serum-derived cosmetic ingredients was similar to the distribution pattern found for anti-elastase activity.

Cosmetic Botanical Ingredient obtained from sage membrane fraction demonstrated potent gelatinase B inhibition activity ($IC_{50}$=24.9 µg/ml) comparable to that of a positive control (rosmarinic acid) having $IC_{50}$=30 µg/ml.

The inhibitory properties of membrane-derived Cosmetic Botanical Ingredients toward gelatinase B indicate that this ingredient has value as an active component of anti-inflammatory topical products.

Example 23

In Vitro Evaluation of Suproxide Scavenging Activity for the Cosmetic Botanical Ingredients Reactive oxygen species generated by activated inflammatory cells (endogenous or exogenous) create specific oxidant which was used to provide the measurements of superoxide scavenging activity. The assay used for evaluation of superoxide scavenging activity relates to the one form of antioxidant activity, which is of benefit in neutralizing the damage associated with oxidation. To generate superoxide anions in high yield and in a controlled fashion, an enzymatic system (xanthine oxidase) was used. The conversion of xanthine to hypoxanthine by this enzyme generates amounts of superoxide anions, which are stoichiometric with the amount of substrate provided. The assay used was based on the reduction of cytochrome c from its ferric to ferrous form as a sensitive measure of superoxide levels. The advantage of using cytochrome c reduction to detect superoxide anions generated by the action of xanthine oxidase on xanthine is that the same measure may be employed to detect the release of superoxide anions by activated inflammatory cells undergoing a "respiratory burst." Cosmetic Botanical Ingredients which decrease the magnitude of the respiratory burst but do not scavenge enzymatically generated superoxide anions are presumably inhibiting some aspect of cell function rather than acting as scavengers of the reactive oxygen species generated by the cells.

The superoxide scavenging data is described below and Tables 35 and 36.

TABLE 35

Evaluation of Superoxide Scavenging Activity of Cosmetic Botanical Ingredients.

| Cosmetic Botanical Ingredient (Source) | $IC_{50}$ µg/ml |
|---|---|
| 101 (Alfalfa Serum Fraction) | 149 |
| 102 (Alfalfa Membrane Fraction) | No Inhibition |
| 201 (Barley Serum Fraction) | 160 |
| 202 (Barley Membrane Fraction) | No Inhibition |
| 301 (Lavender Serum Fraction) | 158 |
| 302 (Lavender Membrane Fraction) | No Inhibition |
| 401 (Marigold Flowers Serum Fraction) | 153 |
| 402 (Marigold Flowers Membrane Fraction) | No Inhibition |
| 501 (Sage Serum Fraction) | >160 |
| 502 (Sage Membrane Fraction) | No Inhibition |
| Positive Control (Rosmarinic Acid) | 26.5 |

Superoxide scavenging ability is fully concentrated in serum-derived cosmetic botanical ingredients. Membrane-derived cosmetic botanical ingredients did not demonstrate any superoxide scavenging ability. The above distribution pattern of superoxide scavenging ability was found for all tested raw material sources.

Serum-derived cosmetic botanical ingredients demonstrated approximately 20% of the superoxide scavenging ability of the positive control (rosmarinic acid).

The superoxide scavenging ability of the serum fractions suggest that these cosmetic botanical ingredients have value as prospective components to act as topical antioxidant and UV-protectant products.

TABLE 36

Evaluation of Superoxide Scavenging Activity of Marigold Products

| Cosmetic Botanical Ingredient or Extract | $IC_{50}$ µg/ml |
|---|---|
| 401 (Marigold Flowers Serum Fractions) | 153 |
| 402 (Marigold Flowers Membrane Fractions) | No Inhibition |
| Commercial Extract (Marigold Flowers) | >160 |
| Conventional Extract (Marigold Flowers) | 53 |

Marigold flowers serum-derived Cosmetic Botanical Ingredient demonstrated significant superoxide scavenging ability, but the membrane-derived Cosmetic Botanical Ingredient (derived from the same raw material) has no detectable inhibition ability.

Commercial extract, which was derived from the same raw material, displayed superoxide scavenging ability which was comparable to that of the serum-derived Cosmetic Botanical Ingredient.

The water extract isolated by conventional methods from the same batch of raw material demonstrated higher superoxide scavenging ability than the serum-derived Cosmetic Botanical Ingredient or the commercial extract.

Example 24

Evaluation of the Effect of Cosmetic Botanical Ingredients on Neutrophil Respiratory Burst The superoxide scavenging activity of different cosmetic botanical ingredients described in the previous Example 23 was measured with an in vitro enzymatically generated source of superoxide anions, and with an in vivo reactive oxygen species generated by activated inflammatory cells (i.e., neutrophils). Neutrophils are especially important sources of reactive oxygen species, because they are involved in greatest numbers to sites of local inflammation and because they convert some of the species, such as superoxide anions and hydrogen peroxide to an antioxidant such as hypochlorous acid. Detection of the superoxide anions which are released into the extracellular environment by neutrophils is a sensitive measure of the overall levels of activity of these cells to generate multiple reactive oxygen species, collectively referred to as the "respiratory burst." The same reagent was employed to detect the extracellular superoxide derived from neutrophils as used to detect superoxide formed enzymatically, i.e., ferricytochrome c. Because this molecule is a protein and cannot enter the neutrophil, it does not detect intracellular reactive oxygen species.

Phorbol myristate acetate (PMA), which is known to mimic the signals for at least two independent pathways for neutrophil activation, was used as a stimulant of respiratory burst in vivo. The rate of cytochrome c reduction by the PMA-activated neutrophils is proportional to the magnitude of the respiratory burst in these cells. Results of dose-dependent inhibition were expressed in terms of the maximal rate of cytochrome c reduction observed after a 150 second lag phase following addition of PMA.

A review of the data regarding the inhibition of neutrophil respiratory burst studies are presented in Table 37.

TABLE 37

Neutrophil Respiratory Burst Evaluation of Cosmetic Botanical Ingredients.

| Cosmetic Botanical Ingredient (Source) and Extract | $V_{max}$ | | | | Dose Response Effect |
|---|---|---|---|---|---|
| | 0 µg/ml | 0.5 µg/ml | 25.0 µg/ml | 50.0 µg/ml | |
| Control (Unstimulated) | 1.96 | — | — | — | — |
| Control (Stimulated) | 18.86 | — | — | — | — |
| 501 (Sage Serum Fraction) | — | 12.11 | 11.0 | 19.0 | Inhibition/Stimulation |
| 401 (Marigold Flowers Serum Fraction) | — | 9.11 | 8.79 | 19.48 | Inhibition/Stimulation |
| Commercial Extract (Marigold Flowers) | — | 15.15 | 11.29 | 10.33 | Only Inhibition |
| Conventional Extract (Marigold Flowers) | — | 21.26 | 10.33 | 8.82 | Only Inhibition |

Both tested Cosmetic Botanical Ingredient 401 and 501 demonstrated biphasic modulation of the respiratory burst from PMA-stimulated neutrophils. At low concentrations, the serum-derived cosmetic botanical ingredients exhibited strong inhibitory activity, but at high concentrations this inhibitory activity was replaced by net modest stimulation of the respiratory burst above that of neutrophils stimulated with PMA alone. Therefore, serum-derived cosmetic botanical ingredients contain components having a stimulatory effect on neutrophils, but these components have only moderate potency, as stimulation is observed only at high concentrations. In addition, the serum-derived cosmetic botanical ingredients contain other components which inhibit the respiratory burst at very low concentrations. The inhibition of the neutrophil respiratory burst at these low concentrations (~2.5 µg dry material/ml) cannot be due simply to superoxide scavenging activity, which required much higher concentrations of dry material (~150 µg/ml) to be detected.

Commercial extract, which was derived from marigold flowers, did not display any stimulatory effect and demonstrated only inhibition of respiratory burst activity.

Water extract isolated by conventional methods from the same batch of marigold flowers as the serum-derived cosmetic botanical ingredient, did not display stimulatory activity. The conventional extract did not retain any of the extremely potent inhibitory activity towards the neutrophil respiratory burst seen at very low (2.5 µg/ml) concentrations of the serum-derived cosmetic botanical ingredients.

Example 25

Protocols Used for Determining Certain Characteristics of Cosmetic Botanical Ingredients 101, 201, 301, 401, 402, 501, and 502

The following are various methods used for determining certain characteristics of Cosmetic Botanical Ingredients 101, 201, 301, 401, 402, 501, and 502. These methods are referenced throughout the above Examples. References below to the "tested products" or the "test samples" refer to Cosmetic Botanical Ingredients 101, 201, 301, 401, 402, 501, and 502.

Method 1: Method for Determination of Solid Content. The procedure for determination of solid content included evaporation of the tested product in the water bath at 100° C. until complete evaporation of water, oven storage of the sample at 105° C. for 3 hours, cooling to room temperature, and immediate determination of the weight of the container with solid matter.

Method 2: Method for Determination of Non-Volatile Residue. The procedure for determination of non-volatile residue included oven storage of the tested product at 105° C. for 5 hours, cooling, and immediate determination of the weight of the container with solid matter.

Method 3: Method for Determination of L*a*b* Values. The procedure for determination of L*a*b* values utilized Hunter Labscan fixed geometry calorimeter with measuring geometry of 0°/450. Standard illuminant $D_{65}$ with viewing window facing upward was used. The container with tested product was placed on viewing window and measured through the bottom. The following CIELAB equations were used:

$$C^* = (a^{*2} + b^{*2})^{1/2}$$

$$DE^* = [(DL)^2 + (Da^*)^2 + (Db^*)^2]^{1/2}$$

$$DH = [(DE^*)^2 - (DL^*)^2 - (DC^*)^2]^{1/2}.$$

Method 4: Method for Determination of Total Carotenoids Content and Lutein Content. The tested samples were extracted with acetone. After homogenization and vacuum filtration, all extracts were saponified with 30% potassium hydroxide in methanol. The carotenoids were successively extracted with petroleum ether. After additional treatment and re-solubilization in ethanol, all samples were measured at 446 nm.

In order to determine the lutein content, an additional dried sample from each sample extraction was used for HPLC analysis. The dried sample was re-solubilized in MTBE and methanol. The reverse phase HPLC system with (250×4.60 mm I.D.) 5 µm $C_{18}$ column ("Vydac") was used. The identity of lutein was conformed by the co-chromatography of an authentic standard. The molar absorptivity coefficient for lutein in ethanol is 144,800 cm$^{-1}$, mol$^{-1}$.

Method 5: Method for Determination of Elastase Inhibitory Activity. The elastase inhibitory activity of tested fractions was determined using the assay, which employs neutrophil elastase (a purified enzyme preparation produced by "Elastin Products") and synthetic peptide soluble substrate Methoxysuccinyl-Ala-Ala-Pro-Val-p-Nitroanilide produced by "Sigma". Enzymatic cleavage of the substrate results in generation of increasing yellow color over time (405 nm); the rate of color generation is diminished by increasing concentrations of tested fractions containing inhibitory activity. Analysis of the concentration dependence of inhibition permits quantitation of the potency of the inhibitory activity, expressed as that concentration of dry matter within each tested fraction required to achieve 50% inhibition ($IC_{50}$), but also provides information relating to the mode of inhibition.

For the determination of $IC_{50}$, the concentration of elastase was 2.5 µg/ml and concentration of substrate was 150 µM. For the determination of $K_i$, the concentrations of substrate were 100 µM and 200 µM.

Method 6: Method for Determination of Gelatinase B Inhibitory Activity. The commercially distributed assay (MMP-9 Activity ELISA produced by "Amersham Pharmacia"), which captures Gelatinase B specifically onto multi-well microplates by immune recognition, was used after other proteinases were washed away. The enzymatic activity was detected at 405 nm by hydrolysis of a low molecular weight synthetic substrate for Gelatinase B: APMA. Analysis of the concentration dependence of inhibition was used to determine the potency of tested product dry matter.

Method 7: Method for Determination of Superoxide Scavenging Activity. The enzymatic system, which uses xanthine oxidase (a purified enzyme preparation produced by "Sigma"), was used to generate superoxide anions in high yield and in a controlled fashion. The conversion of xanthine to hydroxanthine by this enzyme generates amounts of superoxide anions and reduction of ferricytochrome c to ferrocytochrome c was used as a sensitive measure of superoxide levels. The measurements of ferrocytochrome c level (550 nm), when tested fractions were added to the reaction system, allow for determination of their superoxide scavenging activity. The final concentrations per well were for cytochrome c 75 μM, xanthine 425 μm/L, and xanthine oxidase 10 mU/ml.

Method 8: Method for Determination of Inhibition of the Neutrophil Respiratory Burst. The phorbol myristate acetate (PMA produced by Alexis Corporation, San Diego, Calif.) was used as a trigger of the respiratory burst activity demonstrated by neutrophils. The detection of superoxide anions, which are released into the extracellular environment by neutrophils, was achieved via measurements of ferrocytochrome c level. The rate of cytochrome c reduction by PMA-activated neutrophils is proportional to the magnitude of the respiratory burst in these cells. Results of dose-dependent inhibition were expressed in terms of maximal rate of cytochrome c reduction observed at 550 nm after 150 seconds lag phase following addition of PMA.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of preparing a bioactive botanical cosmetic composition, said method comprising:
   providing a plant cell juice, said plant cell juice having been extracted from a fresh plant biomass, wherein said fresh plant biomass is from a plant selected from the group consisting of *Calendula officinalis, Medicago sativa, Lavandula angustifolia, Salvia officinalis* and *Hordeum vulgare;*
   treating the plant cell juice under conditions effective to separate the plant cell juice into a membrane fraction and a cell juice supernatant; and
   converting the membrane fraction under conditions effective to yield a stable bioactive botanical cosmetic composition exhibiting antiproteolytic, cell growth inhibition activity, and/or both antiproteolytic and cell growth inhibition activities, wherein said antiproteolytic activity is due to inhibition of at least one proteinase and said cell growth inhibition activity is due to inhibition of cell growth of at least one type of cell and wherein said converting comprises:
   stabilizing the membrane fraction component by mixing a non-ionic emulsifier and at least one antioxidant with the membrane fraction to yield a stabilized membrane fraction component;
   mixing the stabilized membrane fraction component with a polymer matrix to yield a membrane fraction matrix; and
   neutralizing the membrane fraction matrix to yield a bioactive botanical cosmetic ingredient having antiproteolytic activity, cell growth inhibition activity, or both antiproteolytic and cell growth inhibition activities, wherein said converting is performed prior to any aggregation of the membrane fraction.

2. The method according to claim 1, wherein said treating comprises:
   coagulating the plant cell juice to yield a coagulated cell juice mixture, and
   separating coagulated cell juice mixture to yield a membrane fraction and a cell juice supernatant.

3. The method according to claim 2, wherein said coagulating step comprises:
   destabilizing the cell juice to yield a coagulated cell juice mixture, wherein said destabilizing is achieved through temperature treatment, electro-membrane treatment, chemical treatment and/or their combination.

4. The method according to claim 3, wherein said temperature treatment comprises:
   heating the cell juice extract to a treatment temperature required to induce quantitative coagulation of the membrane fraction, and
   cooling the cell juice to a temperature effective to allow further quantitative separation of said membrane fraction from said cell juice supernatant.

5. The method according to claim 4, wherein said treatment temperature is at 45 to 70 degrees Celsius.

6. The method according to claim 4, wherein said cooling of the heated cell juice is at 30 to 45 degrees Celsius.

7. The method according to claim 4, wherein said separating is carried out by filtration or centrifugation.

8. The method according to claim 1, wherein said polymer matrix comprises at least one polymeric emulsifier and at least one preservative.

9. The method according to claim 1, wherein said neutralizing comprises: adjusting the pH of the membrane fraction matrix to a range of between 2.5 and 6.5.

10. A bioactive botanical cosmetic composition made by the method according to claim 1.

11. The bioactive botanical cosmetic composition according to claim 10, wherein said antiproteolytic activity is indicated by the ability of the bioactive botanical cosmetic composition to inhibit the activity of a proteinase selected from the group consisting of a serine proteinase and a matrix metalloproteinase.

12. The bioactive botanical cosmetic composition according to claim 11, wherein said serine proteinase is neutrophil elastase.

13. The bioactive botanical cosmetic composition according to claim 11, wherein said serine proteinase is trypsin inhibitor.

14. The bioactive botanical cosmetic composition according to claim 11, wherein said matrix metalloproteinase is gelatinase B.

15. The bioactive botanical cosmetic composition according to claim 10, wherein said bioactive botanical cosmetic composition has an antiproteolytic potency ranging from an $IC_{50}$ value of between about 0.1 and about 25.0 μg dry matter/ml, wherein said $IC_{50}$ value represents the concentration of dry matter contained in the membrane fraction required to achieve 50 percent inhibition of said proteinase.

16. The bioactive botanical cosmetic composition according to claim 10, wherein said antiproteolytic activity is reversible.

17. The bioactive botanical cosmetic composition according to claim 10, wherein said bioactive botanical cosmetic composition has a cell growth inhibition potency ranging from an $NRU_{50}$ value of between about 25 and 500 μg dry matter/ml, said $NRU_{50}$ value representing the concentration of dry matter in said membrane fraction required to reduce the viability of said type of cell to 50 percent.

18. A bioactive botanical cosmetic formulation, suitable for topical application to a mammal, comprising a cosmetically acceptable carrier and a cosmetically effective amount of the bioactive botanical cosmetic composition according to claim 10.

19. The cosmetic formulation according to claim 18, wherein the cosmetically acceptable carrier is selected from the group consisting of a hydrophilic cream base, a hydrophilic lotion base, a hydrophilic surfactant base, a hydrophobic cream base, a hydrophobic lotion base, and a hydrophobic surfactant base.

20. The cosmetic formulation according to claim 18, wherein said bioactive botanical cosmetic composition is present in an amount ranging from between about 0.001 percent and about 70 percent of the total weight of the cosmetic formulation.

21. A bioactive botanical cosmetic composition comprising the membrane fraction made by the method according to claim 2.

* * * * *